US010512535B2

(12) United States Patent
Beer

(10) Patent No.: US 10,512,535 B2
(45) Date of Patent: Dec. 24, 2019

(54) DUAL MODE ACCOMMODATIVE-DISACCOMODATIVE INTRAOCULAR LENS

(71) Applicant: Z Lens, LLC, St. Petersburg, FL (US)

(72) Inventor: Paul M. Beer, St. Petersburg, FL (US)

(73) Assignee: Z Lens, LLC, St. Petersburg, FL (US)

(*) Notice: Subject to any disclaimer, the term of this patent is extended or adjusted under 35 U.S.C. 154(b) by 96 days.

(21) Appl. No.: 15/684,313

(22) Filed: Aug. 23, 2017

(65) Prior Publication Data

US 2018/0055626 A1 Mar. 1, 2018

Related U.S. Application Data

(60) Provisional application No. 62/378,737, filed on Aug. 24, 2016.

(51) Int. Cl.
*A61F 2/16* (2006.01)
(52) U.S. Cl.
CPC .......... *A61F 2/1624* (2013.01); *A61F 2/1629* (2013.01); *A61F 2/1635* (2013.01); *A61F 2002/169* (2015.04); *A61F 2002/1682* (2015.04); *A61F 2002/16903* (2015.04); *A61F 2210/0014* (2013.01); *A61F 2230/0026* (2013.01); *A61F 2230/0052* (2013.01)

(58) Field of Classification Search
CPC .... A61F 2/1624; A61F 2/1629; A61F 2/1635; A61F 2002/1682; A61F 2002/169; A61F 2002/16903; A61F 2210/0014; A61F 2230/0052

See application file for complete search history.

(56) References Cited

U.S. PATENT DOCUMENTS

| | | |
|---|---|---|
| 3,975,779 A | 8/1976 | Richards et al. |
| 3,979,780 A | 9/1976 | Boniuk |
| 3,991,426 A | 11/1976 | Flom et al. |
| 4,053,953 A | 10/1977 | Flom et al. |
| 4,056,855 A | 11/1977 | Kelman |
| 4,124,905 A | 11/1978 | Clark |
| 4,149,279 A | 4/1979 | Poler |
| 4,262,370 A | 4/1981 | Hartstein |
| 4,373,218 A | 2/1983 | Schachar |
| 4,463,457 A | 8/1984 | Kelman |

(Continued)

FOREIGN PATENT DOCUMENTS

| | | |
|---|---|---|
| AU | 2003294418 A1 | 6/2004 |
| AU | 2003297101 A1 | 6/2004 |

(Continued)

OTHER PUBLICATIONS

International Search Report and Written Opinion dated Dec. 4, 2013 in International Application No. PCT/US2013/039708.

(Continued)

*Primary Examiner* — David H Willse
*Assistant Examiner* — Tiffany P Shipmon
(74) *Attorney, Agent, or Firm* — Goodwin Procter LLP

(57) ABSTRACT

Embodiments of the invention relate to a flexible, shape-shifting optic adapted to cooperate with a zonular capture haptic system and produce accommodation power both by shape shifting and axial shifting. The optic is designed as a small, thin walled optic vesicle comparable in size to current rigid monofocal IOL optics.

20 Claims, 19 Drawing Sheets

(56) References Cited

U.S. PATENT DOCUMENTS

| | | |
|---|---|---|
| 4,527,294 A | 7/1985 | Heslin |
| 4,534,069 A | 8/1985 | Kelman |
| 4,575,373 A | 3/1986 | Johnson |
| 4,581,032 A | 4/1986 | Grandon |
| 4,581,033 A | 4/1986 | Callahan |
| 4,588,406 A | 5/1986 | Fedorov et al. |
| 4,666,446 A | 5/1987 | Koziol et al. |
| 4,685,922 A | 8/1987 | Peyman |
| 4,693,717 A | 9/1987 | Michelson |
| 4,718,904 A | 1/1988 | Thornton |
| 4,738,680 A | 4/1988 | Herman |
| 4,781,719 A | 11/1988 | Kelman |
| 4,787,903 A | 11/1988 | Grendahl |
| 4,790,847 A | 12/1988 | Woods |
| 4,842,601 A | 6/1989 | Smith |
| 4,871,363 A | 10/1989 | Kelman |
| 4,878,910 A | 11/1989 | Koziol et al. |
| 4,888,012 A | 12/1989 | Horn et al. |
| 4,888,015 A | 12/1989 | Domino |
| 4,892,543 A | 1/1990 | Turley |
| 4,932,966 A | 6/1990 | Christie et al. |
| 4,932,968 A | 6/1990 | Caldwell et al. |
| 4,936,850 A | 6/1990 | Barrett |
| 4,944,082 A | 7/1990 | Jones et al. |
| 4,950,288 A | 8/1990 | Kelman |
| 4,955,894 A | 9/1990 | Herman |
| 4,963,148 A | 10/1990 | Sulc et al. |
| 4,995,879 A | 2/1991 | Dougherty |
| 5,104,590 A | 4/1992 | Blake |
| 5,108,429 A | 4/1992 | Wiley |
| 5,185,107 A | 2/1993 | Blake |
| 5,192,319 A | 3/1993 | Worst |
| RE34,424 E | 10/1993 | Walman |
| 5,282,851 A | 2/1994 | Jacob-LaBarre |
| 5,288,293 A | 2/1994 | O'Donnell, Jr. |
| 5,306,297 A | 4/1994 | Rheinish et al. |
| 5,326,347 A | 7/1994 | Cumming |
| 5,366,500 A | 11/1994 | Schneider et al. |
| 5,423,929 A | 6/1995 | Doyle et al. |
| 5,476,514 A | 12/1995 | Cumming |
| 5,489,302 A | 2/1996 | Skottun |
| 5,496,366 A | 3/1996 | Cumming |
| 5,507,806 A | 4/1996 | Blake |
| 5,527,415 A | 6/1996 | Doyle et al. |
| 5,549,668 A | 8/1996 | O'Donnell, Jr. |
| 5,562,731 A | 10/1996 | Cumming |
| 5,571,177 A | 11/1996 | Deacon et al. |
| 5,578,081 A | 11/1996 | McDonald |
| 5,593,436 A | 1/1997 | Langerman |
| 5,607,472 A | 3/1997 | Thompson |
| 5,674,282 A | 10/1997 | Cumming |
| 5,683,456 A | 11/1997 | Blake |
| 5,702,441 A | 12/1997 | Zhou |
| 5,728,155 A | 3/1998 | Anello et al. |
| 5,728,156 A | 3/1998 | Gupta et al. |
| 5,769,889 A | 6/1998 | Kelman |
| 5,782,911 A | 7/1998 | Herrick |
| 5,800,532 A | 9/1998 | Lieberman |
| 5,803,925 A | 9/1998 | Yang et al. |
| 5,843,187 A | 12/1998 | Bayers |
| 5,855,605 A | 1/1999 | Herrick |
| 5,964,802 A | 10/1999 | Anello et al. |
| 5,984,962 A | 11/1999 | Anello et al. |
| 6,013,101 A | 1/2000 | Israel |
| 6,015,435 A | 1/2000 | Valunin et al. |
| 6,027,531 A | 2/2000 | Tassignon |
| 6,048,364 A | 4/2000 | Skottun |
| 6,051,024 A | 4/2000 | Cumming |
| 6,053,944 A | 4/2000 | Tran et al. |
| 6,083,261 A | 7/2000 | Callahan et al. |
| 6,096,077 A | 8/2000 | Callahan et al. |
| 6,096,078 A | 8/2000 | McDonald |
| 6,110,202 A | 8/2000 | Barraquer et al. |
| 6,139,576 A | 10/2000 | Doyle et al. |
| 6,143,027 A | 11/2000 | Ratner et al. |
| 6,152,959 A | 11/2000 | Portney |
| 6,171,337 B1 | 1/2001 | Galin |
| 6,176,878 B1 | 1/2001 | Gwon et al. |
| 6,179,843 B1 | 1/2001 | Weiler |
| 6,190,410 B1 | 2/2001 | Lamielle et al. |
| 6,197,058 B1 | 3/2001 | Portney |
| 6,197,059 B1 | 3/2001 | Cumming |
| 6,200,342 B1 | 3/2001 | Tassignon |
| 6,200,344 B1 | 3/2001 | Lamielle et al. |
| 6,217,612 B1 | 4/2001 | Woods |
| 6,224,628 B1 | 5/2001 | Callahan et al. |
| 6,228,115 B1 | 5/2001 | Hoffmann et al. |
| 6,241,777 B1 | 6/2001 | Kellan |
| 6,251,312 B1 | 6/2001 | Phan et al. |
| 6,261,321 B1 | 7/2001 | Kellan |
| 6,280,449 B1 | 8/2001 | Blake |
| 6,299,641 B1 | 10/2001 | Woods |
| 6,302,912 B1 | 10/2001 | Bernau |
| 6,306,167 B1 | 10/2001 | Bernau et al. |
| 6,358,280 B1 | 3/2002 | Herrick |
| 6,387,126 B1 | 5/2002 | Cumming |
| 6,398,809 B1 | 6/2002 | Hoffmann et al. |
| 6,406,494 B1 | 6/2002 | Laguette et al. |
| 6,413,262 B2 | 7/2002 | Saishin et al. |
| 6,413,277 B1 | 7/2002 | Neuhann |
| 6,423,094 B1 | 7/2002 | Sarfarazi |
| 6,425,917 B1 | 7/2002 | Blake |
| 6,428,574 B1 | 8/2002 | Valunin et al. |
| 6,432,246 B1 | 8/2002 | Blake |
| 6,443,984 B1 | 9/2002 | Jahn et al. |
| 6,443,985 B1 | 9/2002 | Woods |
| 6,451,056 B1 | 9/2002 | Cumming |
| 6,461,384 B1 | 10/2002 | Hoffmann et al. |
| 6,464,725 B2 | 10/2002 | Skotton |
| 6,475,240 B1 | 11/2002 | Paul |
| 6,482,229 B1 | 11/2002 | Gwon et al. |
| 6,488,707 B1 | 12/2002 | Callahan et al. |
| 6,488,708 B2 | 12/2002 | Sarfarazi |
| 6,488,709 B1 | 12/2002 | Barrett |
| 6,494,911 B2 | 12/2002 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,537,317 B1 | 3/2003 | Steinert et al. |
| 6,543,453 B1 | 4/2003 | Klima et al. |
| 6,547,822 B1 | 4/2003 | Lang |
| 6,554,859 B1 | 4/2003 | Lang et al. |
| 6,558,395 B2 | 5/2003 | Hjertman et al. |
| 6,558,420 B2 | 5/2003 | Green |
| 6,576,012 B2 | 6/2003 | Lang |
| 6,592,621 B1 | 7/2003 | Domino |
| 6,596,025 B2 | 7/2003 | Portney |
| 6,605,093 B1 | 8/2003 | Blake |
| 6,616,692 B1 | 9/2003 | Glick et al. |
| 6,638,306 B2 | 10/2003 | Cumming |
| 6,660,035 B1 | 12/2003 | Lang et al. |
| 6,666,887 B1 | 12/2003 | Callahan et al. |
| 6,695,881 B2 | 2/2004 | Peng et al. |
| 6,730,123 B1 | 5/2004 | Klopotek |
| 6,749,634 B2 | 6/2004 | Hanna |
| 6,755,859 B2 | 6/2004 | Hoffmann et al. |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,928 B2 | 9/2004 | Callahan et al. |
| 6,786,934 B2 | 9/2004 | Zadno-Azizi et al. |
| 6,790,232 B1 | 9/2004 | Lang |
| 6,797,003 B1 | 9/2004 | Blake et al. |
| 6,800,091 B2 | 10/2004 | Callahan et al. |
| 6,824,563 B2 | 11/2004 | Lang |
| 6,836,374 B2 | 12/2004 | Esch et al. |
| 6,846,326 B2 | 1/2005 | Zadno-Azizi et al. |
| 6,849,091 B1 | 2/2005 | Cumming |
| 6,855,164 B2 | 2/2005 | Glazier |
| 6,858,040 B2 | 2/2005 | Nguyen et al. |
| 6,860,601 B2 | 3/2005 | Shadduck |
| 6,884,261 B2 | 4/2005 | Zadno-Azizi et al. |
| 6,899,732 B2 | 5/2005 | Zadno-Azizi et al. |
| 6,918,930 B2 | 7/2005 | Portney |

(56) References Cited

U.S. PATENT DOCUMENTS

| | | |
|---|---|---|
| 6,921,415 B2 | 7/2005 | Callahan et al. |
| 6,921,416 B2 | 7/2005 | Khoury |
| 6,926,736 B2 | 8/2005 | Peng et al. |
| 6,926,744 B1 | 8/2005 | Bos et al. |
| 6,932,839 B1 | 8/2005 | Kamerling et al. |
| 6,935,743 B2 | 8/2005 | Shadduck |
| 6,966,649 B2 | 11/2005 | Shadduck |
| 6,969,403 B2 | 11/2005 | Peng et al. |
| 6,986,763 B2 | 1/2006 | Holmen |
| 6,986,787 B1 | 1/2006 | Baker, Jr. |
| 6,991,651 B2 | 1/2006 | Portney |
| 7,025,783 B2 | 4/2006 | Brady et al. |
| 7,036,931 B2 | 5/2006 | Lindacher et al. |
| 7,037,338 B2 | 5/2006 | Nagamoto |
| 7,041,134 B2 | 5/2006 | Nguyen et al. |
| 7,048,759 B2 | 5/2006 | Bogaert et al. |
| 7,048,760 B2 | 5/2006 | Cumming |
| 7,060,094 B2 | 6/2006 | Shahinpoor et al. |
| 7,063,723 B2 | 6/2006 | Ran |
| 7,068,439 B2 | 6/2006 | Esch et al. |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 * | 10/2006 | Esch ............... A61F 2/1616 623/6.13 |
| 7,125,422 B2 | 10/2006 | Woods et al. |
| 7,137,702 B2 | 11/2006 | Piers et al. |
| 7,150,759 B2 | 12/2006 | Paul et al. |
| 7,150,760 B2 | 12/2006 | Zhang |
| 7,192,444 B2 | 3/2007 | Blake et al. |
| 7,198,640 B2 | 4/2007 | Nguyen |
| 7,204,849 B2 | 4/2007 | Portney |
| 7,217,288 B2 | 5/2007 | Esch et al. |
| 7,220,279 B2 | 5/2007 | Nun |
| 7,226,478 B2 | 6/2007 | Ting et al. |
| 7,229,475 B2 | 6/2007 | Glazier |
| 7,238,201 B2 | 7/2007 | Portney et al. |
| 7,247,168 B2 | 7/2007 | Esch et al. |
| 7,261,737 B2 | 8/2007 | Esch et al. |
| 7,264,351 B2 | 9/2007 | Shadduck |
| 7,278,739 B2 | 10/2007 | Shadduck |
| 7,354,451 B2 | 4/2008 | Koch |
| 7,377,640 B2 | 5/2008 | Piers et al. |
| 7,381,221 B2 | 6/2008 | Lang et al. |
| 7,384,429 B2 | 6/2008 | Hanna |
| 7,404,637 B2 | 7/2008 | Miller et al. |
| 7,404,638 B2 | 7/2008 | Miller et al. |
| 7,435,259 B2 | 10/2008 | Cumming |
| 7,438,723 B2 | 10/2008 | Esch |
| 7,452,362 B2 | 11/2008 | Zadno-Azizi et al. |
| 7,452,378 B2 | 11/2008 | Zadno-Azizi et al. |
| 7,455,691 B2 | 11/2008 | Feingold et al. |
| 7,462,193 B2 | 12/2008 | Nagamoto |
| 7,485,144 B2 | 2/2009 | Esch |
| 7,494,505 B2 | 2/2009 | Kappelhof et al. |
| 7,503,938 B2 | 3/2009 | Phillips |
| 7,553,327 B2 | 6/2009 | Cumming |
| 7,569,073 B2 | 8/2009 | Vaudant et al. |
| 7,591,849 B2 | 9/2009 | Richardson |
| 7,601,169 B2 | 10/2009 | Phillips |
| 7,615,056 B2 | 11/2009 | Ayton et al. |
| 7,615,073 B2 | 11/2009 | Deacon et al. |
| 7,621,949 B2 | 11/2009 | Deacon et al. |
| 7,637,947 B2 | 12/2009 | Smith et al. |
| 7,662,179 B2 | 2/2010 | Sarfarazi |
| 7,670,371 B2 | 3/2010 | Piers et al. |
| 7,674,288 B2 | 3/2010 | Nagamoto |
| 7,713,299 B2 | 5/2010 | Brady et al. |
| 7,722,670 B2 | 5/2010 | Elahi et al. |
| 7,744,646 B2 | 6/2010 | Zadno-Azizi et al. |
| 7,744,647 B2 | 6/2010 | Barrett |
| 7,763,069 B2 | 7/2010 | Brady et al. |
| 7,763,070 B2 | 7/2010 | Cumming |
| 7,771,471 B2 | 8/2010 | Dell |
| 7,776,088 B2 | 8/2010 | Shadduck |
| 7,780,729 B2 | 8/2010 | Nguyen et al. |
| 7,790,824 B2 | 9/2010 | Freeman |
| 7,790,825 B2 | 9/2010 | Lehman et al. |
| 7,794,497 B2 | 9/2010 | Brady et al. |
| 7,794,498 B2 | 9/2010 | Pinchuk |
| 7,806,930 B2 | 10/2010 | Brown |
| 7,811,320 B2 | 10/2010 | Werblin |
| 7,815,678 B2 | 10/2010 | Ben Nun |
| 7,837,730 B2 | 11/2010 | Cumming et al. |
| 7,842,087 B2 | 11/2010 | Ben Nun |
| 7,854,764 B2 | 12/2010 | Ben Nun |
| 7,857,850 B2 | 12/2010 | Mentak et al. |
| 7,871,437 B2 | 1/2011 | Hermans et al. |
| 7,878,655 B2 | 2/2011 | Salvati et al. |
| 7,883,540 B2 | 2/2011 | Niwa et al. |
| 7,905,917 B2 | 3/2011 | Altmann |
| 7,931,686 B2 | 4/2011 | Vaudant et al. |
| 7,942,889 B2 | 5/2011 | Assia |
| 7,981,155 B2 | 7/2011 | Cumming |
| 7,985,253 B2 | 7/2011 | Cumming |
| 7,998,198 B2 | 8/2011 | Angelopoulos et al. |
| 7,998,199 B2 | 8/2011 | Ben Nun |
| 8,012,204 B2 | 9/2011 | Weinschenk, III et al. |
| 8,034,106 B2 | 10/2011 | Mentak et al. |
| 8,034,107 B2 | 10/2011 | Stenger |
| 8,034,108 B2 | 10/2011 | Bumbalough |
| 8,038,711 B2 | 10/2011 | Clarke |
| 8,043,370 B2 | 10/2011 | Bretthauer et al. |
| 8,043,372 B2 | 10/2011 | Bumbalough |
| 8,048,155 B2 | 11/2011 | Shadduck |
| 8,048,156 B2 | 11/2011 | Geraghty et al. |
| 8,052,752 B2 | 11/2011 | Woods et al. |
| 8,062,361 B2 | 11/2011 | Nguyen et al. |
| 8,062,362 B2 | 11/2011 | Brady et al. |
| 8,066,768 B2 | 11/2011 | Werblin |
| 8,066,769 B2 | 11/2011 | Werblin |
| 8,070,806 B2 | 12/2011 | Khoury |
| 8,080,017 B2 | 12/2011 | Tanaka |
| 8,100,965 B2 | 1/2012 | Cumming et al. |
| 8,109,998 B2 | 2/2012 | Cumming |
| 8,123,729 B2 | 2/2012 | Yamamoto et al. |
| 8,133,273 B2 | 3/2012 | Aharoni et al. |
| 8,158,712 B2 | 4/2012 | Your |
| 8,163,015 B2 | 4/2012 | Cumming |
| 8,167,941 B2 | 5/2012 | Boyd et al. |
| 8,182,531 B2 | 5/2012 | Hermans et al. |
| 8,187,325 B2 | 5/2012 | Zadno-Azizi et al. |
| 8,206,442 B2 | 6/2012 | Sel et al. |
| 8,215,770 B2 | 7/2012 | Blum et al. |
| 8,216,305 B2 | 7/2012 | Salvati et al. |
| 8,216,306 B2 | 7/2012 | Coroneo |
| 8,216,308 B2 | 7/2012 | Blake et al. |
| 8,231,672 B2 | 7/2012 | Deacon et al. |
| 8,235,525 B2 | 8/2012 | Lesage et al. |
| 8,241,353 B2 | 8/2012 | Deacon et al. |
| 8,241,355 B2 | 8/2012 | Brady et al. |
| 8,246,679 B2 | 8/2012 | Nguyen et al. |
| 8,267,996 B2 | 9/2012 | Niwa et al. |
| 8,273,123 B2 | 9/2012 | Ben Nun |
| 8,303,656 B2 | 11/2012 | Shadduck |
| 8,314,927 B2 | 11/2012 | Choi et al. |
| 8,328,869 B2 | 12/2012 | Smiley et al. |
| 8,343,216 B2 | 1/2013 | Brady et al. |
| 8,343,217 B2 | 1/2013 | Bumbalough |
| 8,349,006 B2 | 1/2013 | Zhao et al. |
| 8,357,196 B2 | 1/2013 | Jain et al. |
| 8,361,145 B2 | 1/2013 | Scholl et al. |
| 8,366,653 B2 | 2/2013 | Shareef et al. |
| 8,377,123 B2 | 2/2013 | Evans et al. |
| 8,377,125 B2 | 2/2013 | Kellan |
| 8,382,831 B2 | 2/2013 | Ben Nun |
| 8,382,832 B2 | 2/2013 | Deacon et al. |
| 8,398,709 B2 | 3/2013 | Ben Nun |
| 8,403,984 B2 | 3/2013 | Tsai et al. |
| 8,414,646 B2 | 4/2013 | De Juan, Jr. et al. |
| 8,425,595 B2 | 4/2013 | Tsai et al. |
| 8,425,597 B2 | 4/2013 | Glick et al. |
| 8,425,598 B2 | 4/2013 | Klink et al. |

(56) References Cited

U.S. PATENT DOCUMENTS

| | | |
|---|---|---|
| 8,425,599 B2 | 4/2013 | Shadduck |
| 8,430,928 B2 | 4/2013 | Liao |
| 8,435,289 B2 | 5/2013 | Cole et al. |
| 8,447,086 B2 | 5/2013 | Hildebrand et al. |
| 8,449,611 B2 | 5/2013 | Richardson |
| 8,454,688 B2 | 6/2013 | Esch et al. |
| 8,465,544 B2 | 6/2013 | Brady et al. |
| 8,475,527 B2 | 7/2013 | Peterson et al. |
| 8,475,529 B2 | 7/2013 | Clarke |
| 8,480,734 B2 | 7/2013 | Kellan et al. |
| 8,486,140 B2 | 7/2013 | Willis et al. |
| 8,486,141 B2 | 7/2013 | Lang et al. |
| 8,486,142 B2 | 7/2013 | Bumbalough et al. |
| 8,496,701 B2 | 7/2013 | Hermans et al. |
| 8,500,804 B2 | 8/2013 | Brady et al. |
| 8,500,806 B1 | 8/2013 | Phillips |
| 8,523,942 B2 | 9/2013 | Cumming |
| 8,529,623 B2 | 9/2013 | Piers et al. |
| 8,535,376 B2 | 9/2013 | Altmann |
| 8,545,556 B2 | 10/2013 | Woods et al. |
| 8,551,164 B2 | 10/2013 | Willis et al. |
| 8,551,167 B2 | 10/2013 | Cuevas |
| 8,556,967 B2 | 10/2013 | Sarfarazi |
| 8,562,674 B2 | 10/2013 | Cole et al. |
| 8,568,478 B2 | 10/2013 | Zickler et al. |
| 8,574,293 B2 | 11/2013 | Kappelhof et al. |
| 8,579,971 B2 | 11/2013 | Webb |
| 8,579,972 B2 | 11/2013 | Rombach |
| 8,585,758 B2 | 11/2013 | Woods |
| 8,585,759 B2 | 11/2013 | Bumbalough |
| 8,608,799 B2 | 12/2013 | Blake |
| 8,608,800 B2 | 12/2013 | Portney |
| 8,613,766 B2 | 12/2013 | Richardson et al. |
| 8,623,082 B2 | 1/2014 | Kappelhof et al. |
| 8,647,384 B2 | 2/2014 | Lu |
| 8,652,206 B2 | 2/2014 | Masket |
| 8,657,877 B2 | 2/2014 | Glazier |
| 8,657,878 B2 | 2/2014 | Mentak et al. |
| 8,668,734 B2 | 3/2014 | Hildebrand et al. |
| 8,900,298 B2 | 12/2014 | Anvar et al. |
| 8,956,408 B2 | 2/2015 | Smiley et al. |
| 8,968,396 B2 | 3/2015 | Matthews et al. |
| 8,992,609 B2 | 3/2015 | Shadduck |
| 9,044,317 B2 | 6/2015 | Hildebrand et al. |
| 9,072,600 B2 | 7/2015 | Tran |
| 9,186,244 B2 | 11/2015 | Silvestrini et al. |
| 9,220,590 B2 | 12/2015 | Beer |
| 9,277,987 B2 | 3/2016 | Smiley et al. |
| 9,364,318 B2 | 6/2016 | Beer |
| 9,456,895 B2 | 10/2016 | Shadduck |
| 9,610,155 B2 | 4/2017 | Matthews |
| 9,693,858 B2 | 7/2017 | Hildebrand et al. |
| 9,795,473 B2 | 10/2017 | Smiley et al. |
| 9,855,137 B2 | 1/2018 | Smiley et al. |
| 9,855,139 B2 | 1/2018 | Matthews et al. |
| 9,872,762 B2 | 1/2018 | Scholl et al. |
| 9,872,763 B2 | 1/2018 | Smiley et al. |
| 10,004,596 B2 | 6/2018 | Brady et al. |
| 10,045,844 B2 | 8/2018 | Smiley et al. |
| 10,111,745 B2 | 10/2018 | Silvestrini et al. |
| 10,159,564 B2 | 12/2018 | Brady et al. |
| 10,195,020 B2 | 2/2019 | Matthews |
| 2001/0001836 A1 | 5/2001 | Cumming |
| 2001/0012964 A1 | 8/2001 | Lang et al. |
| 2001/0016771 A1 | 8/2001 | Cumming |
| 2001/0044657 A1 | 11/2001 | Kellan |
| 2001/0051826 A1 | 12/2001 | Bogaert et al. |
| 2002/0002404 A1 | 1/2002 | Sarfarazi |
| 2002/0013622 A1 | 1/2002 | Hennig |
| 2002/0016630 A1 | 2/2002 | Lang |
| 2002/0045937 A1 | 4/2002 | Sarfarazi |
| 2002/0051063 A1 | 5/2002 | Hwang |
| 2002/0072673 A1 | 6/2002 | Yamamoto et al. |
| 2002/0072795 A1 | 6/2002 | Green |
| 2002/0101564 A1 | 8/2002 | Herrick |
| 2002/0103535 A1 | 8/2002 | Portney |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0116062 A1 | 8/2002 | Portney |
| 2002/0133228 A1 | 9/2002 | Sarver |
| 2002/0138140 A1 | 9/2002 | Hanna |
| 2002/0138141 A1 | 9/2002 | Zadno-Azizi et al. |
| 2002/0143395 A1 | 10/2002 | Skottun |
| 2002/0161435 A1 | 10/2002 | Portney |
| 2002/0173847 A1 | 11/2002 | Pham et al. |
| 2002/0177896 A1 | 11/2002 | Israel |
| 2002/0183843 A1 | 12/2002 | Blake et al. |
| 2002/0193876 A1 | 12/2002 | Lang et al. |
| 2002/0193877 A1 | 12/2002 | Hoffmann et al. |
| 2003/0018386 A1 | 1/2003 | Laguette et al. |
| 2003/0033011 A1 | 2/2003 | Singer et al. |
| 2003/0033013 A1 | 2/2003 | Callahan et al. |
| 2003/0060878 A1 | 3/2003 | Shadduck |
| 2003/0065387 A1 | 4/2003 | Callahan et al. |
| 2003/0074060 A1 | 4/2003 | Zadno-Azizi et al. |
| 2003/0074061 A1 | 4/2003 | Pham et al. |
| 2003/0078655 A1 | 4/2003 | Callahan et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0093149 A1 | 5/2003 | Glazier |
| 2003/0105522 A1 | 6/2003 | Glazier |
| 2003/0109926 A1 | 6/2003 | Portney |
| 2003/0114927 A1 | 6/2003 | Nagamoto |
| 2003/0130732 A1 | 7/2003 | Sarfarazi |
| 2003/0135271 A1 | 7/2003 | Bandhauer |
| 2003/0135273 A1 | 7/2003 | Callahan et al. |
| 2003/0147046 A1 | 8/2003 | Shadduck |
| 2003/0149480 A1 | 8/2003 | Shadduck |
| 2003/0171808 A1 | 9/2003 | Phillips |
| 2003/0171809 A1 | 9/2003 | Phillips |
| 2003/0181977 A1 | 9/2003 | Brady |
| 2003/0187504 A1 | 10/2003 | Weinschenk et al. |
| 2003/0199976 A1 | 10/2003 | Portney |
| 2003/0204254 A1 | 10/2003 | Peng et al. |
| 2003/0204255 A1 | 10/2003 | Peng et al. |
| 2003/0204256 A1 | 10/2003 | Peng et al. |
| 2004/0015236 A1 | 1/2004 | Sarfarazi et al. |
| 2004/0034417 A1 | 2/2004 | Heyman |
| 2004/0064182 A1 | 4/2004 | Kelman |
| 2004/0073304 A1 | 4/2004 | Weinschenk, III et al. |
| 2004/0082993 A1 | 4/2004 | Woods |
| 2004/0082994 A1 | 4/2004 | Woods et al. |
| 2004/0082995 A1 | 4/2004 | Woods |
| 2004/0100704 A1 | 5/2004 | Shadduck |
| 2004/0106992 A1 | 6/2004 | Lang et al. |
| 2004/0106993 A1 | 6/2004 | Portney |
| 2004/0111152 A1 | 6/2004 | Kelman |
| 2004/0111153 A1 | 6/2004 | Woods et al. |
| 2004/0117013 A1 | 6/2004 | Schachar |
| 2004/0158322 A1 | 8/2004 | Shen |
| 2004/0162612 A1 | 8/2004 | Portney et al. |
| 2004/0169816 A1 | 9/2004 | Esch |
| 2004/0169932 A1 | 9/2004 | Esch et al. |
| 2004/0181279 A1 | 9/2004 | Nun |
| 2004/0184158 A1 | 9/2004 | Shadduck |
| 2004/0190153 A1 | 9/2004 | Esch |
| 2004/0215340 A1 | 10/2004 | Messner et al. |
| 2004/0230300 A1 | 11/2004 | Bandhauer et al. |
| 2004/0236422 A1 | 11/2004 | Zhang et al. |
| 2004/0236423 A1 | 11/2004 | Zhang et al. |
| 2004/0243233 A1 | 12/2004 | Phillips |
| 2004/0249455 A1 | 12/2004 | Tran |
| 2005/0021137 A1 | 1/2005 | Blake et al. |
| 2005/0021138 A1 | 1/2005 | Woods |
| 2005/0021139 A1 | 1/2005 | Shadduck |
| 2005/0049700 A1 | 3/2005 | Zadno-Azizi et al. |
| 2005/0055092 A1 | 3/2005 | Nguyen et al. |

(56) References Cited

U.S. PATENT DOCUMENTS

| | | |
|---|---|---|
| 2005/0060032 A1 | 3/2005 | Magnante et al. |
| 2005/0071002 A1 | 3/2005 | Glazier |
| 2005/0075732 A1 | 4/2005 | Israel |
| 2005/0085907 A1 | 4/2005 | Hanna |
| 2005/0090896 A1 | 4/2005 | Ben Nun |
| 2005/0096741 A1 | 5/2005 | Cumming |
| 2005/0107873 A1 | 5/2005 | Zhou |
| 2005/0107875 A1 | 5/2005 | Cumming |
| 2005/0113914 A1 | 5/2005 | Miller et al. |
| 2005/0119739 A1 | 6/2005 | Glazier |
| 2005/0119740 A1 | 6/2005 | Esch et al. |
| 2005/0125055 A1 | 6/2005 | Deacon et al. |
| 2005/0125057 A1 | 6/2005 | Cumming |
| 2005/0125059 A1 | 6/2005 | Pinchuk et al. |
| 2005/0131535 A1 | 6/2005 | Woods |
| 2005/0137703 A1 | 6/2005 | Chen |
| 2005/0143814 A1 | 6/2005 | Esch et al. |
| 2005/0149183 A1 | 7/2005 | Shadduck |
| 2005/0149184 A1 | 7/2005 | Bogaert |
| 2005/0209692 A1 | 9/2005 | Zhang |
| 2005/0234547 A1 | 10/2005 | Nguyen et al. |
| 2005/0251254 A1 | 11/2005 | Brady et al. |
| 2005/0267575 A1 | 12/2005 | Nguyen et al. |
| 2006/0020339 A1 | 1/2006 | Ran |
| 2006/0030938 A1 | 2/2006 | Altmann |
| 2006/0041307 A1 | 2/2006 | Esch et al. |
| 2006/0047339 A1 | 3/2006 | Brown |
| 2006/0047340 A1 | 3/2006 | Brown |
| 2006/0061729 A1 | 3/2006 | Shadduck |
| 2006/0064162 A1 | 3/2006 | Klima |
| 2006/0069433 A1 | 3/2006 | Nun |
| 2006/0087614 A1 | 4/2006 | Shadduck |
| 2006/0089712 A1 | 4/2006 | Malecaze |
| 2006/0092340 A1 | 5/2006 | Blum et al. |
| 2006/0100701 A1 | 5/2006 | Esch et al. |
| 2006/0100703 A1 | 5/2006 | Evans et al. |
| 2006/0100704 A1 | 5/2006 | Blake et al. |
| 2006/0116765 A1 | 6/2006 | Blake et al. |
| 2006/0142855 A1 | 6/2006 | Vaudant et al. |
| 2006/0149369 A1 | 7/2006 | Cumming et al. |
| 2006/0178741 A1 | 8/2006 | Zadno-Azizi et al. |
| 2006/0178742 A1 | 8/2006 | Nagamoto |
| 2006/0184244 A1 | 8/2006 | Nguyen et al. |
| 2006/0212116 A1 | 9/2006 | Woods |
| 2006/0212117 A1 | 9/2006 | Lang et al. |
| 2006/0247766 A1 | 11/2006 | Marin |
| 2006/0247767 A1 | 11/2006 | Koch |
| 2006/0253196 A1 | 11/2006 | Woods |
| 2006/0259139 A1 | 11/2006 | Zadno-Azizi et al. |
| 2006/0259140 A1 | 11/2006 | Dell |
| 2006/0271186 A1 | 11/2006 | Nishi et al. |
| 2006/0271187 A1 | 11/2006 | Zadno-Azizi et al. |
| 2007/0005135 A1 | 1/2007 | Makker et al. |
| 2007/0005136 A1 | 1/2007 | Richardson |
| 2007/0010880 A1 | 1/2007 | Esch |
| 2007/0010882 A1 | 1/2007 | Barrett |
| 2007/0016293 A1 | 1/2007 | Tran |
| 2007/0021831 A1 | 1/2007 | Clarke |
| 2007/0021832 A1 | 1/2007 | Nordan |
| 2007/0027540 A1 | 2/2007 | Zadno-Azizi et al. |
| 2007/0032866 A1 | 2/2007 | Portney |
| 2007/0050024 A1 | 3/2007 | Zhang |
| 2007/0050025 A1 | 3/2007 | Nguyen et al. |
| 2007/0067030 A1 | 3/2007 | Glazier et al. |
| 2007/0078515 A1 | 4/2007 | Brady |
| 2007/0083260 A1 | 4/2007 | Colvard |
| 2007/0083261 A1 | 4/2007 | Colvard |
| 2007/0088433 A1 | 4/2007 | Esch et al. |
| 2007/0100444 A1 | 5/2007 | Brady et al. |
| 2007/0100445 A1 | 5/2007 | Shadduck |
| 2007/0106377 A1 | 5/2007 | Smith et al. |
| 2007/0106380 A1 | 5/2007 | Terwee et al. |
| 2007/0106381 A1 | 5/2007 | Blake |
| 2007/0108643 A1 | 5/2007 | Zadno-Azizi et al. |
| 2007/0118216 A1 | 5/2007 | Pynson |
| 2007/0123981 A1 | 5/2007 | Tassignon |
| 2007/0129798 A1 | 6/2007 | Chawdhary |
| 2007/0129803 A1 | 6/2007 | Cumming et al. |
| 2007/0135915 A1 | 6/2007 | Klima |
| 2007/0142913 A1 | 6/2007 | Phillips |
| 2007/0156236 A1 | 7/2007 | Stenger |
| 2007/0171366 A1 | 7/2007 | Su et al. |
| 2007/0185574 A1 | 8/2007 | Ben Nun |
| 2007/0203578 A1 | 8/2007 | Scholl et al. |
| 2007/0213817 A1 | 9/2007 | Esch et al. |
| 2007/0239274 A1 | 10/2007 | Kellan |
| 2007/0244560 A1 | 10/2007 | Ossipov et al. |
| 2007/0244561 A1 | 10/2007 | Ben Nun |
| 2007/0260308 A1 | 11/2007 | Tran |
| 2007/0260309 A1 | 11/2007 | Richardson |
| 2007/0260310 A1 | 11/2007 | Richardson |
| 2007/0270946 A1 | 11/2007 | Poley |
| 2007/0299487 A1 | 12/2007 | Shadduck |
| 2008/0004699 A1 | 1/2008 | Ben Nun |
| 2008/0015689 A1 | 1/2008 | Esch et al. |
| 2008/0021549 A1 | 1/2008 | Eagan et al. |
| 2008/0021550 A1 | 1/2008 | Richardson |
| 2008/0033449 A1 | 2/2008 | Cole et al. |
| 2008/0046074 A1 | 2/2008 | Smith et al. |
| 2008/0046075 A1 | 2/2008 | Esch et al. |
| 2008/0046076 A1 | 2/2008 | Rombach |
| 2008/0051801 A1 | 2/2008 | Hovey et al. |
| 2008/0077238 A1 | 3/2008 | Deacon et al. |
| 2008/0077239 A1 | 3/2008 | Zickler et al. |
| 2008/0086206 A1 | 4/2008 | Nasiatka et al. |
| 2008/0086208 A1 | 4/2008 | Nordan |
| 2008/0109077 A1 | 5/2008 | Bos |
| 2008/0109078 A1 | 5/2008 | Rozakis et al. |
| 2008/0154364 A1 | 6/2008 | Richardson et al. |
| 2008/0161913 A1 | 7/2008 | Brady et al. |
| 2008/0161914 A1 | 7/2008 | Brady et al. |
| 2008/0183289 A1 | 7/2008 | Werblin |
| 2008/0188930 A1 | 8/2008 | Mentak et al. |
| 2008/0200982 A1 | 8/2008 | Your |
| 2008/0208335 A1 | 8/2008 | Blum et al. |
| 2008/0215147 A1 | 9/2008 | Werblin |
| 2008/0243247 A1 | 10/2008 | Poley et al. |
| 2008/0269642 A1 | 10/2008 | Deacon et al. |
| 2008/0269882 A1 | 10/2008 | Simpson et al. |
| 2008/0269885 A1 | 10/2008 | Simpson et al. |
| 2008/0269886 A1 | 10/2008 | Simpson et al. |
| 2008/0281417 A1 | 11/2008 | Nagamoto |
| 2008/0300680 A1 | 12/2008 | Joshua |
| 2008/0306587 A1 | 12/2008 | Your |
| 2008/0306588 A1 | 12/2008 | Smiley et al. |
| 2009/0005865 A1 | 1/2009 | Smiley et al. |
| 2009/0005866 A1 | 1/2009 | Cumming |
| 2009/0012609 A1 | 1/2009 | Geraghty et al. |
| 2009/0018652 A1 | 1/2009 | Hermans et al. |
| 2009/0027661 A1 | 1/2009 | Choi et al. |
| 2009/0030425 A1 | 1/2009 | Smiley et al. |
| 2009/0033863 A1 | 2/2009 | Blum et al. |
| 2009/0036982 A1 | 2/2009 | Aharoni et al. |
| 2009/0062912 A1 | 3/2009 | Rombach |
| 2009/0124773 A1 | 5/2009 | Zhou et al. |
| 2009/0125105 A1 | 5/2009 | Lesage et al. |
| 2009/0125106 A1 | 5/2009 | Weinschenk, III et al. |
| 2009/0149952 A1 | 6/2009 | Shadduck |
| 2009/0171458 A1 | 7/2009 | Kellan et al. |
| 2009/0187242 A1 | 7/2009 | Weeber et al. |
| 2009/0198326 A1 | 8/2009 | Zhou et al. |
| 2009/0204209 A1 | 8/2009 | Tran |
| 2009/0204210 A1 | 8/2009 | Pynson |
| 2009/0204211 A1 | 8/2009 | Angelopoulos et al. |
| 2009/0210054 A1 | 8/2009 | Weeber et al. |
| 2009/0228101 A1 | 9/2009 | Zadno-Azizi |
| 2009/0234448 A1 | 9/2009 | Weeber et al. |
| 2009/0234449 A1 | 9/2009 | De Juan, Jr. et al. |
| 2009/0248152 A1 | 10/2009 | Bumbalough |
| 2009/0248154 A1 | 10/2009 | Dell |
| 2009/0264998 A1 | 10/2009 | Mentak et al. |
| 2009/0264999 A1 | 10/2009 | Cumming |
| 2009/0265000 A1 | 10/2009 | Vaudant et al. |
| 2009/0292354 A1 | 11/2009 | Gontijo et al. |

(56) References Cited

U.S. PATENT DOCUMENTS

| | | |
|---|---|---|
| 2009/0292355 A1 | 11/2009 | Boyd et al. |
| 2009/0312836 A1 | 12/2009 | Pinchuk et al. |
| 2009/0319040 A1 | 12/2009 | Khoury |
| 2010/0016964 A1 | 1/2010 | Werblin |
| 2010/0036490 A1 | 2/2010 | Deacon et al. |
| 2010/0094412 A1 | 4/2010 | Wensrich |
| 2010/0094415 A1 | 4/2010 | Bumbalough |
| 2010/0121443 A1 | 5/2010 | Michel et al. |
| 2010/0121444 A1 | 5/2010 | Ben Nun |
| 2010/0131058 A1 | 5/2010 | Shadduck |
| 2010/0131059 A1 | 5/2010 | Callahan et al. |
| 2010/0131061 A1 | 5/2010 | Callahan et al. |
| 2010/0134754 A1 | 6/2010 | Hong et al. |
| 2010/0137983 A1 | 6/2010 | Culbertson et al. |
| 2010/0152848 A1 | 6/2010 | Williamson et al. |
| 2010/0179652 A1 | 7/2010 | Yamamoto et al. |
| 2010/0179653 A1 | 7/2010 | Argento et al. |
| 2010/0198349 A1 | 8/2010 | Brady et al. |
| 2010/0204788 A1 | 8/2010 | Van Noy |
| 2010/0211167 A1 | 8/2010 | Glazier |
| 2010/0211170 A1 | 8/2010 | Liao |
| 2010/0211171 A1 | 8/2010 | Sarfarazi |
| 2010/0228260 A1 | 9/2010 | Callahan et al. |
| 2010/0228344 A1 | 9/2010 | Shadduck |
| 2010/0228346 A1 | 9/2010 | Esch |
| 2010/0292789 A1 | 11/2010 | Willis et al. |
| 2010/0318186 A1 | 12/2010 | Bumbalough et al. |
| 2010/0324671 A1 | 12/2010 | Shadduck |
| 2010/0324672 A1 | 12/2010 | Esch et al. |
| 2010/0324673 A1 | 12/2010 | Nguyen et al. |
| 2011/0029074 A1 | 2/2011 | Reisin et al. |
| 2011/0035001 A1 | 2/2011 | Woods |
| 2011/0035002 A1 | 2/2011 | Nun |
| 2011/0040376 A1 | 2/2011 | Christie et al. |
| 2011/0040378 A1 | 2/2011 | Werblin |
| 2011/0040379 A1 | 2/2011 | Bumbalough |
| 2011/0052020 A1 | 3/2011 | Hildebrand et al. |
| 2011/0054600 A1 | 3/2011 | Bumbalough |
| 2011/0054601 A1 | 3/2011 | Kadziauskas et al. |
| 2011/0071628 A1 | 3/2011 | Gross et al. |
| 2011/0082544 A1 | 4/2011 | Ben Nun |
| 2011/0093067 A1 | 4/2011 | Michalek et al. |
| 2011/0098810 A1 | 4/2011 | Altmann |
| 2011/0098812 A1 | 4/2011 | Ben Nun |
| 2011/0112635 A1 | 5/2011 | Ben Nun |
| 2011/0112636 A1 | 5/2011 | Ben Nun |
| 2011/0112638 A1 | 5/2011 | Hermans et al. |
| 2011/0118836 A1 | 5/2011 | Jain et al. |
| 2011/0153014 A1 | 6/2011 | Zhang et al. |
| 2011/0153015 A1 | 6/2011 | Simonov et al. |
| 2011/0160852 A1 | 6/2011 | Mentak et al. |
| 2011/0184514 A1 | 7/2011 | Angelopoulos et al. |
| 2011/0191086 A1 | 8/2011 | Callahan et al. |
| 2011/0208301 A1 | 8/2011 | Anvar et al. |
| 2011/0224788 A1 | 9/2011 | Webb |
| 2011/0238174 A1 | 9/2011 | Hong et al. |
| 2011/0245920 A1 | 10/2011 | Richardson |
| 2011/0251686 A1 | 10/2011 | Masket |
| 2011/0257742 A1 | 10/2011 | Bumbalough et al. |
| 2011/0270389 A1 | 11/2011 | Glazer et al. |
| 2011/0282441 A1 | 11/2011 | Zadno-Azizi |
| 2011/0282442 A1 | 11/2011 | Scholl et al. |
| 2011/0282443 A1 | 11/2011 | Smiley et al. |
| 2011/0288638 A1 | 11/2011 | Smiley et al. |
| 2011/0295368 A1 | 12/2011 | Betser |
| 2011/0304058 A1 | 12/2011 | Pendse |
| 2011/0307058 A1* | 12/2011 | Beer .................. A61F 2/1629 623/6.43 |
| 2011/0313522 A1 | 12/2011 | Hayes |
| 2011/0313523 A1 | 12/2011 | Hayes |
| 2012/0010704 A1 | 1/2012 | Bumbalough |
| 2012/0016473 A1 | 1/2012 | Brady et al. |
| 2012/0022547 A1 | 1/2012 | Hildebrand et al. |
| 2012/0029632 A1 | 2/2012 | Ben Nun |
| 2012/0035724 A1 | 2/2012 | Clarke |
| 2012/0046743 A1 | 2/2012 | Pinchuk |
| 2012/0046744 A1 | 2/2012 | Woods et al. |
| 2012/0059465 A1 | 3/2012 | Brady et al. |
| 2012/0078361 A1 | 3/2012 | Shadduck |
| 2012/0078363 A1 | 3/2012 | Lu |
| 2012/0078364 A1 | 3/2012 | Stenger |
| 2012/0116506 A1 | 5/2012 | Compertore |
| 2012/0130487 A1 | 5/2012 | Doraiswamy et al. |
| 2012/0130488 A1 | 5/2012 | Doraiswamy et al. |
| 2012/0143327 A1 | 6/2012 | Bumbalough |
| 2012/0150292 A1 | 6/2012 | Mentak et al. |
| 2012/0203338 A1 | 8/2012 | Jain |
| 2012/0232648 A1 | 9/2012 | Kahook et al. |
| 2012/0232650 A1 | 9/2012 | Hermans et al. |
| 2012/0232651 A1 | 9/2012 | Kahook et al. |
| 2012/0245591 A1 | 9/2012 | Matthews |
| 2012/0245684 A1 | 9/2012 | Liao |
| 2012/0253458 A1 | 10/2012 | Geraghty et al. |
| 2012/0253459 A1 | 10/2012 | Reich et al. |
| 2012/0290084 A1 | 11/2012 | Coroneo |
| 2012/0296425 A1 | 11/2012 | Cumming |
| 2012/0296426 A1 | 11/2012 | Brady et al. |
| 2012/0303119 A1 | 11/2012 | Callahan et al. |
| 2012/0310338 A1 | 12/2012 | Christie et al. |
| 2012/0310342 A1 | 12/2012 | Nguyen et al. |
| 2012/0310343 A1 | 12/2012 | Van Noy |
| 2012/0310344 A1 | 12/2012 | Cumming |
| 2012/0310345 A1 | 12/2012 | Olcina Portilla |
| 2012/0323320 A1 | 12/2012 | Simonov et al. |
| 2012/0323321 A1 | 12/2012 | Simonov et al. |
| 2012/0330415 A1 | 12/2012 | Callahan et al. |
| 2013/0013060 A1 | 1/2013 | Zadno-Azizi et al. |
| 2013/0018461 A1 | 1/2013 | Ben Nun |
| 2013/0030525 A1 | 1/2013 | Brady et al. |
| 2013/0035760 A1 | 2/2013 | Portney |
| 2013/0053954 A1 | 2/2013 | Rao et al. |
| 2013/0060330 A1 | 3/2013 | Weeber et al. |
| 2013/0060331 A1 | 3/2013 | Shadduck |
| 2013/0060332 A1 | 3/2013 | Simpson |
| 2013/0073039 A1 | 3/2013 | Mirlay |
| 2013/0103146 A1 | 4/2013 | Smiley et al. |
| 2013/0103147 A1 | 4/2013 | Christie et al. |
| 2013/0110235 A1 | 5/2013 | Schwiegerling |
| 2013/0116781 A1 | 5/2013 | Ben Nun |
| 2013/0131794 A1 | 5/2013 | Smiley et al. |
| 2013/0138208 A1 | 5/2013 | Simonov et al. |
| 2013/0150961 A1 | 6/2013 | Evans et al. |
| 2013/0166026 A1 | 6/2013 | Bumbalough |
| 2013/0184816 A1 | 7/2013 | Hayes |
| 2013/0190868 A1 | 7/2013 | Kahook et al. |
| 2013/0197635 A1 | 8/2013 | Phillips |
| 2013/0204364 A1 | 8/2013 | Olson |
| 2013/0204365 A1 | 8/2013 | Dell |
| 2013/0226294 A1 | 8/2013 | Van Der Mooren et al. |
| 2013/0226295 A1 | 8/2013 | de Juan, Jr. et al. |
| 2013/0231741 A1 | 9/2013 | Clarke |
| 2013/0231742 A1 | 9/2013 | Deacon et al. |
| 2013/0238091 A1 | 9/2013 | Danta et al. |
| 2013/0245754 A1 | 9/2013 | Blum et al. |
| 2013/0245756 A1 | 9/2013 | Liao |
| 2013/0250239 A1 | 9/2013 | Hildebrand et al. |
| 2013/0268070 A1 | 10/2013 | Esch et al. |
| 2013/0268071 A1 | 10/2013 | Vilupuru et al. |
| 2013/0282117 A1 | 10/2013 | Van Heugten et al. |
| 2013/0297018 A1 | 11/2013 | Brady et al. |
| 2013/0304202 A1 | 11/2013 | Basinger |
| 2013/0304203 A1* | 11/2013 | Beer .................. A61F 2/1624 623/6.37 |
| 2013/0304204 A1 | 11/2013 | Bumbalough et al. |
| 2013/0310931 A1 | 11/2013 | Kahook et al. |
| 2013/0310932 A1 | 11/2013 | Kellan |
| 2013/0317606 A1 | 11/2013 | Culbertson et al. |
| 2013/0317608 A1 | 11/2013 | Hermans et al. |
| 2013/0331937 A1 | 12/2013 | Stevens |
| 2013/0338767 A1 | 12/2013 | Mazzocchi et al. |
| 2013/0345713 A1 | 12/2013 | Cole et al. |
| 2014/0005780 A1 | 1/2014 | Zhao |
| 2014/0005781 A1 | 1/2014 | Zhao et al. |
| 2014/0005782 A1 | 1/2014 | Kellan et al. |

(56) References Cited

U.S. PATENT DOCUMENTS

| | | |
|---|---|---|
| 2014/0012277 A1 | 1/2014 | Matthews et al. |
| 2014/0052245 A1 | 2/2014 | Zickler et al. |
| 2014/0052246 A1 | 2/2014 | Kahook et al. |
| 2014/0058507 A1 | 2/2014 | Reich et al. |
| 2014/0142588 A1 | 5/2014 | Hildebrand et al. |
| 2014/0180403 A1 | 6/2014 | Silvestrini et al. |
| 2014/0180405 A1 | 6/2014 | Weinschenk, III et al. |
| 2014/0180406 A1 | 6/2014 | Simpson |
| 2014/0180407 A1 | 6/2014 | Sohn et al. |
| 2014/0194859 A1 | 7/2014 | Ianchulev |
| 2014/0249625 A1 | 9/2014 | Shadduck |
| 2015/0087743 A1 | 3/2015 | Anvar et al. |
| 2015/0088254 A1 | 3/2015 | Cumming |
| 2015/0105760 A1 | 4/2015 | Rao et al. |
| 2015/0134059 A1 | 5/2015 | Curatu |
| 2015/0142108 A1 | 5/2015 | Akura et al. |
| 2015/0202041 A1 | 7/2015 | Shadduck |
| 2015/0238310 A1 | 8/2015 | Matthews et al. |
| 2015/0257874 A1 | 9/2015 | Hildebrand et al. |
| 2016/0030161 A1 | 2/2016 | Brady et al. |
| 2016/0038278 A1 | 2/2016 | Matthews |
| 2016/0128826 A1 | 5/2016 | Silvestrini et al. |
| 2016/0157996 A1 | 6/2016 | Dolla et al. |
| 2016/0184091 A1 | 6/2016 | Smiley et al. |
| 2016/0184092 A1 | 6/2016 | Smiley et al. |
| 2016/0262875 A1 | 9/2016 | Smith et al. |
| 2016/0317286 A1 | 11/2016 | Brady et al. |
| 2016/0317287 A1 | 11/2016 | Silvestrini et al. |
| 2016/0361157 A1 | 12/2016 | Honigsbaum |
| 2017/0020662 A1 | 1/2017 | Shadduck |
| 2017/0049561 A1 | 2/2017 | Smiley et al. |
| 2017/0079773 A1 | 3/2017 | Matthews et al. |
| 2017/0247525 A1 | 8/2017 | Silvestrini et al. |
| 2017/0290658 A1 | 10/2017 | Hildebrand et al. |
| 2017/0342096 A1 | 11/2017 | Silvestrini |
| 2018/0028308 A1 | 2/2018 | Smiley et al. |
| 2018/0125640 A1 | 5/2018 | Smiley et al. |
| 2018/0147051 A1 | 5/2018 | Scholl et al. |
| 2018/0153682 A1 | 6/2018 | Hajela et al. |
| 2018/0177639 A1 | 6/2018 | Rao et al. |
| 2018/0256315 A1 | 9/2018 | Hildebrand et al. |
| 2018/0271645 A1 | 9/2018 | Brady et al. |
| 2018/0344453 A1 | 12/2018 | Brady et al. |
| 2019/0000612 A1 | 1/2019 | Rao et al. |
| 2019/0099263 A1 | 4/2019 | Brady et al. |

FOREIGN PATENT DOCUMENTS

| | | |
|---|---|---|
| AU | 2003300879 A1 | 7/2004 |
| AU | 2004211746 A1 | 8/2004 |
| AU | 2004219674 A1 | 9/2004 |
| AU | 2005299661 A1 | 5/2006 |
| AU | 2006265668 A1 | 1/2007 |
| AU | 2006304339 A1 | 4/2007 |
| AU | 2007340043 A1 | 7/2008 |
| AU | 2008218313 A1 | 8/2008 |
| AU | 2008279167 A1 | 1/2009 |
| AU | 2008279173 A1 | 1/2009 |
| AU | 2010235988 A1 | 11/2010 |
| AU | 2010203427 A1 | 7/2011 |
| AU | 2012335677 A1 | 5/2014 |
| AU | 2014202532 A1 | 7/2014 |
| AU | 2013235467 A1 | 9/2014 |
| AU | 2015258287 A1 | 12/2015 |
| AU | 2017216460 A1 | 8/2017 |
| AU | 2016275073 A1 | 1/2018 |
| AU | 2018200978 A1 | 3/2018 |
| AU | 2016349532 A1 | 4/2018 |
| AU | 2019201556 A1 | 3/2019 |
| CA | 2506753 A1 | 6/2004 |
| CA | 2508143 A1 | 6/2004 |
| CA | 2507694 A1 | 7/2004 |
| CA | 2515355 A1 | 8/2004 |
| CA | 2584472 A1 | 5/2006 |
| CA | 2613580 A1 | 1/2007 |
| CA | 2626269 A1 | 4/2007 |
| CA | 2674816 A1 | 7/2008 |
| CA | 2676713 A1 | 8/2008 |
| CA | 2693906 A1 | 1/2009 |
| CA | 2696450 A1 | 1/2009 |
| CA | 2748812 A1 | 7/2010 |
| CA | 2854919 A1 | 5/2013 |
| CA | 2865954 A1 | 9/2013 |
| CA | 2987311 A1 | 12/2016 |
| CA | 3001477 A1 | 5/2017 |
| DE | 112010004191 T5 | 11/2012 |
| EP | 1563337 A2 | 8/2005 |
| EP | 1569581 A1 | 9/2005 |
| EP | 1585563 A2 | 10/2005 |
| EP | 1590702 A2 | 11/2005 |
| EP | 1599748 A2 | 11/2005 |
| EP | 1816984 A2 | 8/2007 |
| EP | 1906882 A2 | 4/2008 |
| EP | 1948084 A2 | 7/2008 |
| EP | 2053991 A2 | 5/2009 |
| EP | 2094193 A2 | 9/2009 |
| EP | 2112932 A2 | 11/2009 |
| EP | 2178462 A2 | 4/2010 |
| EP | 2178463 A2 | 4/2010 |
| EP | 2178464 A2 | 4/2010 |
| EP | 2221024 A1 | 8/2010 |
| EP | 2384167 A2 | 11/2011 |
| EP | 2473138 A2 | 7/2012 |
| EP | 2539351 A2 | 1/2013 |
| EP | 2559405 A2 | 2/2013 |
| EP | 2563275 A1 | 3/2013 |
| EP | 2647353 A1 | 10/2013 |
| EP | 2671541 A1 | 12/2013 |
| EP | 2688515 A2 | 1/2014 |
| EP | 2775961 A1 | 9/2014 |
| EP | 2827804 A1 | 1/2015 |
| EP | 2934383 A1 | 10/2015 |
| EP | 2967842 A1 | 1/2016 |
| EP | 3049023 A1 | 8/2016 |
| EP | 3062741 A1 | 9/2016 |
| EP | 3062742 A1 | 9/2016 |
| EP | 3174500 A1 | 6/2017 |
| EP | 3181094 A1 | 6/2017 |
| EP | 3197462 A1 | 8/2017 |
| EP | 3263574 A1 | 1/2018 |
| EP | 3307206 A1 | 4/2018 |
| EP | 3370647 A1 | 9/2018 |
| EP | 3383320 A1 | 10/2018 |
| GB | 1583193 A | 1/1981 |
| HK | 1227277 A | 10/2017 |
| HK | 1227679 A | 10/2017 |
| HK | 1234303 A | 2/2018 |
| HK | 1235658 A | 3/2018 |
| HK | 1239501 A | 5/2018 |
| HK | 1241712 A | 6/2018 |
| HK | 1242207 A | 6/2018 |
| IN | 6305DELNP2015 A | 7/2016 |
| IN | 201617018083 A | 8/2016 |
| IN | 201717013927 A | 8/2017 |
| IN | 201617044673 A | 2/2018 |
| JP | 2014061387 A | 4/2014 |
| NL | 2012420 A | 9/2014 |
| WO | WO-2004046768 A2 | 6/2004 |
| WO | WO-2004052242 A1 | 6/2004 |
| WO | WO-2004054471 A2 | 7/2004 |
| WO | WO-2004072689 A2 | 8/2004 |
| WO | WO-2006047383 A2 | 5/2006 |
| WO | WO-2007005778 A2 | 1/2007 |
| WO | WO-2007047529 A2 | 4/2007 |
| WO | WO-2007047530 A2 | 4/2007 |
| WO | WO-2008024766 A2 | 2/2008 |
| WO | WO-2008077040 A2 | 6/2008 |
| WO | WO-2008082957 A2 | 7/2008 |
| WO | WO-2008103798 A2 | 8/2008 |
| WO | WO-2009015161 A2 | 1/2009 |
| WO | WO-2009015226 A2 | 1/2009 |
| WO | WO-2009015234 A2 | 1/2009 |
| WO | WO-2009015240 A2 | 1/2009 |
| WO | WO-2010081093 A2 | 7/2010 |

(56) References Cited

FOREIGN PATENT DOCUMENTS

| WO | WO-2011026068 A2 | 3/2011 |
| WO | WO-2011106435 A2 | 9/2011 |
| WO | WO-2011137191 A1 | 11/2011 |
| WO | WO-2012006616 A2 | 1/2012 |
| WO | WO-20120106673 A1 | 8/2012 |
| WO | WO-2012129407 A2 | 9/2012 |
| WO | WO-2013070924 A1 | 5/2013 |
| WO | WO-2013142323 A1 | 9/2013 |
| WO | WO-2013166068 A1 | 11/2013 |
| WO | WO-2014099630 A1 | 6/2014 |
| WO | WO-2014134302 A1 | 9/2014 |
| WO | WO-2014145562 A1 | 9/2014 |
| WO | WO-2015148673 A1 | 10/2015 |
| WO | WO-2016018932 A1 | 2/2016 |
| WO | WO-2016049059 A1 | 3/2016 |
| WO | WO-2016201351 A1 | 12/2016 |
| WO | WO-2017079733 A1 | 5/2017 |
| WO | WO-2017085344 A1 | 5/2017 |

OTHER PUBLICATIONS

Invitation to Pay Additional Fees dated Sep. 17, 2013 in International Application No. PCT/US2013/039708.

International Preliminary Report on Patentability and Written Opinion dated Nov. 20, 2014 in International Application No. PCT/US2013/039708 (13 pages).

Communication Pursuant to Rule 164(2) and Article 94(3) dated Oct. 11, 2018, for Application No. 13725509.7, 9 pg.

International Search Report and Written Opinion in PCT/US2017/048219 dated Jan. 2, 2018, 19 pages.

Communication Pursuant to Article 94(3) EPC dated Oct. 11, 2018 in European Patent Application No. 13725509.7, 9 pages.

Communication Pursued to Article 94(3) EPC dated Apr. 2, 2019 in European Patent Application No. 17772509.0, 3 pages.

* cited by examiner

DUAL MODE ACCOMMODATIVE-DISACCOMODATIVE INTRAOCULAR LENS

RELATED APPLICATION

This application claims priority to and the benefit of U.S. Provisional Patent Application Ser. No. 62/378,737 filed on Aug. 24, 2016, the disclosure of which is hereby incorporated by reference in its entirety.

FIELD OF THE INVENTION

Embodiments of the present invention relate generally to intraocular lenses. More particularly, embodiments of the invention relate to accommodative and disaccommodative intraocular lens systems (AD-IOL) and a shape shifting flexible optic adapted to couple with a zonular capture haptic system. The combined features of this flexible optic and zonular capture system haptic system result in a novel, dual mode AD-IOL in which the optic shifts both in shape and in position inside the eye, mimicking the behavior of the natural lens, with the small optic adapted to function in the closed and fibrosed capsular bag that results from conventional cataract surgery.

BACKGROUND

Under normal conditions, a healthy human eye focuses on near and distant objects by contraction and relaxation of the ciliary muscle thereby contracting and releasing the tension on the zonules in the eye. The elastic forces of the eye cause disaccommodation and the elastic recoil of the lens caused accommodation. The balance between these two opposing elastic forces is modulated by the neurologically controlled contraction of the ciliary body. The contraction of the ciliary muscle releases zonular tension (accommodative state) and allows the lens to return to a more globular or spherical resting shape. The relaxation of the ciliary muscle increases tension on zonules and elastic forces in the eye tissue overcome the inherent lens elasticity and result in stretching the lens equator and flattening the lens curvature (disaccommodative state).

In certain instances, for example when age-related opacification of the lens (cataract) interferes with vision, the natural crystalline lens of the eye needs to be removed. Generally, the natural lens is replaced with an artificial one, for example, an intraocular lens (IOL).

Unfortunately, conventional IOLs, and currently FDA approved accommodative IOLs, may be unable to provide sufficient spatial displacement of the lens along the optical axis to provide an adequate amount of accommodation for near vision. For an accommodative IOL to be effective, it preferably provides equally for both accommodation and disaccommodation.

In conventional extracapsular cataract surgery, the crystalline lens matrix is removed by phacoemulsification through a curvilinear capsularhexis leaving intact the thin walls of the anterior and posterior capsules, together with zonular ligament connections to the ciliary body and ciliary muscles. An intraocular lens is then placed in the capsular bag, which collapses around the IOL. A conventional monofocal IOL is rigidly fixated in the nonmoving and fibrosed capsular bag. The position of the IOL in the capsular bag is neither in the accommodated or disaccommodated state, but somewhere in between, as determined by the amount of bag contraction and IOL design. This position is called "effective lens position" and it is utilized in calculating the power of the desired optic. The power of the optic determines the single point of perfectly focused vision, often selected at a practical arm length range.

Conventional axial shifting accommodative intraocular lenses (AIOL) rely on the interaction of the ciliary muscle with the zonule and capsule and the vitreous fluid compartment to induce movement of the optic of the AIOL along its optical axis. Typically, the AIOL is secured within the capsular bag that attempts to translate both the rotational and the radial stretching force exerted by the zonules in an attempt to achieve the desired axial displacement of the optic.

However, during the post-implantation fibrotic healing process, the anterior capsule fuses with the posterior capsule to form a rigid capsular disc, a strait jacket for the AIOL. Loss of elasticity of the capsular disc results and constrains the amount of movement, both centrifugal and rotational, that can be generated by the eye disaccommodation forces transmitted to the IOL via zonules or by the elastic recoil of the intraocular lens within the bag and therefore, leads to a decrease in the amount of axial displacement of the lens that can be achieved. The lens neither accommodates nor disaccommodates.

Various lens systems have been designed to address this loss of accommodation. One type of passive-shift single-optic lens, the only accommodative lens currently marketed in the United States, was designed to move forward under vitreous humor pressure when presumably the ciliary muscle contracts and forces vitreous forward. Even the limited amount of accommodative amplitudes generated by this lens immediately after surgery may be lost within the first few weeks or month after surgery as capsular fibrosis ensues and sometimes the movement is backwards. No passive shift AIOLs are marketed in the US that translate ciliary muscle contraction into forward shift of the optic by direct mechanical action of the haptics.

Accommodative lens designs with single or multiple optic lens assemblies have been disclosed, for example, in U.S. Patent Publication Nos. 2009/0125106, 2005/0209692, 2007/0156236, 2009/0005866, 2007/0005136, and 2009/0248154. Dual optic lenses retain the problem of capsular fibrosis and loss of amplitude/movement even though they are theoretically expected to provide a significant amount of accommodation. One such IOL received regulatory approval in Europe, but was abandoned and withdrawn from the market because of poor and unpredictable clinical results. This lens did not receive FDA approval and currently this approach appears to have been abandoned.

More recently, a lens systems that employs an active-shift mechanism using repulsive mini-magnets as a means of making accommodation partially independent of the zonules and mechanical properties of the capsular bag was disclosed (see U.S. Patent Publication Nos. 2009/0204210 and 2007/0118216). Still other methods of achieving accommodation include introduction of a polymerizable fluid with a desired refractive index into the capsular bag (lens refilling). Extensive investigation into the feasibility of these methods is still needed.

U.S. Patent Publication No. 2009/0234449 discloses an intraocular lens having an accommodating element that is in contact with a substantial portion of the zonular contact region of the ciliary body; the accommodating element is positioned relative to optical element and configured to cooperate with the ciliary muscle, the zonules and/or the vitreous pressure in the eye to effect a shape change to the optical element. According to the '449 publication, prior art multiple lens systems can be cumbersome and may also require an axial displacement unachievable with a collapsed capsular bag and resulting ineffective accommodative mechanisms.

More recently, a lens system has been described that employs a novel zonular capture haptic (ZCH) (see U.S. Patent Publication No. 2011/0307058, incorporated herein by reference in its entirety). The lens system provides improved accommodation via a two stage procedure. In the implantation step, Stage 1, a specially designed sectionable haptic, i.e., a ZCH, is inserted between the anterior and posterior lens capsules and it is maintained in a restrained configuration. Sufficient time is allowed for fusion and fibrosis of the two capsule leaflets to each other, thereby permanently trapping the haptic components between the capsules. During Stage 2, activation surgery may be subsequently performed to section the fused capsular bag between individual haptic components and release the restraining mechanism, thereby breaking the mechanical restraint that typically limits movement of other "in the bag" implanted IOLs.

SUMMARY

The basis for embodiments of the present invention is an accommodative-disaccommodative IOL (AD-IOL) with flexible shape shifting optic and zonular capture haptics having a dual mode of action: both an axial shift of the optic and a shape shift of the optic, driven by the dynamic balance between the action of the zonular capture haptics on the flexible optic and the shape memory of the optic and or haptic system. Embodiments of the present invention assemble together numerous individual elements, some that have been previously described separately as components of different modality IOLs, into a novel, comprehensive, and cohesive design. This unique design is specifically constructed to function in a closed and fibrosed capsular bag as is encountered after conventional cataract surgery, and results in an AD-IOL having a size similar to that of conventional IOLs. The shape shifting of the optic allows for a far greater range of accommodation than provided by the axial shift component alone. Both components act synergistically to increase the amount of accommodation obtained. The unavoidable biological response of healing and scarring after cataract surgery is not avoided, but rather utilized for the proper function of this dual mode AD IOL, which is actuated by the radial pull of the zonules. In contrast, the prior art describes attempts to prevent closure of the bag and to use the unfused capsules, open bag, to compress mechanical structures that transmit force to various optic designs, or to use the direct compression of the ciliary muscle.

The ratio between the volume and surface area of a shape shifting flexible optic changes as the optic geometry changes from accommodated to disaccommodated configuration. Embodiments of the dual mode AD-IOL described herein are adapted to alter this ratio in several ways so that the optic can attain its required degree of sphericity.

The AD-IOL enables both accommodation and disaccommodation to take place under the force load produced by zonules in the post-surgical fibrosed capsular bag, specifically as it has been measured and verified experimentally. The balance between accommodation and disaccommodation is controlled by the ciliary muscle and is transmitted via zonules, as a radial pull, to the zonular capture components of the haptic system and then to the AD-IOL system. The AD-IOL responds to the disaccommodative force exercised on it by zonules that counter the inherent accommodative elasticity of the AD-IOL, which is configured to return to a fully accommodated configuration at rest. The ciliary body contraction can then modulate the disaccommodation force exercised on the AD-IOL by zonules in a measured way under neural control, thereby allowing the AD-IOL to assume in a desired configuration based on the balance of accommodation and disaccommodation forces. The zonular capture haptics have been previously described in U.S. Patent Publication No. 2011/0307058. Embodiments of the present invention include an intraocular lens system that includes a shape-shifting flexible optic, i.e., an optic of variable power in which the power can be changed by the forces of accommodation or disaccommodation produced in the eye and that can return to the original power when these forces subside. It may also include a zonular capture haptic system. The shape-shifting flexible optic may include a small, fluid-filled, elastic thin walled optic vesicle, with characteristics adapted to be altered by action of haptics attached thereto. In use, the optic vesicle may be acted upon by the action of the haptic system during accommodation or disaccommodation. This action alters the shape of the optic vesicle thereby changing its dioptric power.

Both the optic and the haptic system may have shape memory that is calculated to generate elastic recoil of the AD-IOL to the accommodated state when zonular tension is reduced. The shape memory features of the haptic and/or optic systems cooperate to result in the ability of the AD-IOL to respond to the actual small forces generated inside the eye subsequent to cataract surgery and capsular bag closure and fibrosis.

In an aspect, embodiments of the invention relate to a dual mode accommodative-disaccommodative intraocular lens (dual mode AD-IOL) including a haptic system having a plurality of closed-loop haptics having shape memory. A shape-shifting flexible optic includes an anterior optic capsule and a posterior optic capsule, each of the two capsules having a fusion zone and the fusion zones of the two capsules being fused together, thereby defining therebetween an optic vesicle, the optic vesicle being filled with a fluid. The haptics are attached to the optic, allowing an action of the haptics to alter a shape of the optic, The shape-shifting flexible optic has a diameter of ≤8 mm. The dual mode AD-IOL, at rest, is in a fully accommodated configuration as a result of at least one of the shape memory of the haptic system and a shape-shifting capability of the flexible optic. A restraining component is sized and configured to immobilize the haptic in at least one of a flatter angle and a larger diameter in a disaccommodated configuration of the AD-IOL, when compared to the accommodated configuration.

One or more of the following features may be included. The closed-loop haptics may be at least one of trapezoidal and T-shaped. The dual-mode AD-IOL may include an optic ring that connects the haptics to each other and to the optic. The haptics may be attached to the optic by a portion of each haptic being embedded in the optic at the fusion zone. Each closed-loop haptic may be configured to adapted to transmit to the optic radial pull created by zonular tension during disaccommodation of the AD-IOL. Each closed-loop haptic may be configured to adapted to return to a set shape during accommodation of the AD-IOL.

The restraining component may be a restraining tab disposed on a haptic or an optic ring, a restraining hole defined by a haptic portion, a restraining hole defined by an optic in a fusion zone thereof, a cross bar on a haptic arm, a restraining ring, and/or a suture.

A ring-shaped plate may be embedded between an anterior optic capsule and a posterior optic capsule of the optic. The ring-shaped plate may define at least one concentric ring of holes. The ring-shaped plate may include a material having shape memory. The ring-shaped plate (i) may be more rigid than the optic and (ii) may provide structural stability to the optic. The ring-shaped plate may include a non-reflective surface.

Each of the closed-loop haptics may include a sinusoidal-shaped equatorial portion. Each of the closed-loop haptics may include a first connecting feature and the optic may include a second connecting feature adapted to engage with the first connecting feature.

The first connecting feature may be a ring defined by each of the closed-loop haptics, the second connecting feature may include a plurality of pegs defined by the optic, and each ring may be sized and configured to receive a peg.

The first connecting feature may include a T defined by each of the closed-loop haptics, and the second connecting feature may include a T-shaped groove defined by the optic and sized and configured to receive each T. Each of the closed-loop haptics may be shape set to contribute to axial shift and shape shift of the optic.

The plurality of closed-loop haptics may be defined by a continuous loop configured to change diameter in response a change of diameter of a capsular bag in which the dual-mode AD-IOL is implanted, thereby diminishing irregular tension on the optic from zonules.

Each of the closed-loop haptics may include spaced-apart ends proximate the optic, thereby enabling expansion of the closed-loop haptics.

The haptic system may include at least two optic rings, each optic ring including two closed-loop haptics, the optic rings being disposed over the optic and configured to rotate to overlay the haptics of a first optic ring over the haptics of a proximate optic ring, to reduce a profile thereof to facilitate loading of the dual-mode AD-IOL in an injector.

At least one closed-loop haptic may include a radial segment and a paddle being disposed on the radial segment configured to compress a portion of the optic.

A sum of accommodative memory of the optic and the haptic system may be accommodative at rest.

A sum of at least an accommodative memory or a disaccommodative memory of the optic and the haptic system may be less than 1 gram force. A sum of at least an accommodative memory or a disaccommodative memory of the optic and the haptic system may be less than zonular tension.

The anterior and posterior optic capsules may be fused with a bonding material and the fusion zone may define a channel configured to receive excess bonding material.

A change in a shape of the flexible optic may change a ratio of a surface area of the optic vesicle to a volume of the optic vesicle changes and the haptic system may change size and shape to accommodate the change in the ratio.

One of the optic capsules may have a thick, rigid optical zone carrying a fixed refractive power including astigmatic correction. An axis of the rigid optical zone may be marked externally. The rigid optical zone may function as a centration and fixation zone to the haptic system.

One of the optic capsules may include a thinner, more easily distorted flexion zone disposed proximate a central optical zone. One of the optic capsules may have thicker, less easily distorted piston zones disposed within or proximate to the flexion zone optic zone and adapted to push fluid toward the center of the optic vesicle. The thicker piston zone may include a plurality of structures adapted to capture and affix radial arms of the haptic system.

Each fusion zone may be adapted to embed individual haptics of the haptic system.

The optic vesicle may be filled with a constant volume of the fluid at no more than a minimally stretched configuration, to cause minimal resistance to shape shifting.

The optic vesicle may have shape memory.

The fluid may have an index of refraction greater than an index of refraction of water, e.g., substantially the same as an index of refraction of the optic vesicle.

The haptic system may be adapted to fit within an IOL injection system, e.g., adapted to roll into a cylinder.

The AD-IOL may be adapted to be restrained in a flattened, stretched out, disaccommodated configuration at implantation and during capsular bag fusion and fibrosis.

The AD-IOL may be adapted to be released by an external laser application. The external laser application may section simultaneously both the restraining device and the fused capsular bag of an eye at the same time by radial cuts between haptics, the radial cuts extending from edges of the eye's anterior capsule towards an equator of the eye's capsular bag for a distance defined to produce a desired amount of release in stiffness of the eye's fibrosed capsular bag.

In another aspect, embodiments of the invention relate to a method for implanting a dual-mode AD-IOL. The method includes providing an AD-IOL including a haptic system having a plurality of closed-loop haptics having shape memory. A shape-shifting flexible optic includes an anterior optic capsule and a posterior optic capsule, each of the two capsules having a fusion zone and the fusion zones of the two capsules being fused together, thereby defining therebetween an optic vesicle, the optic vesicle being filled with a fluid. The haptics are attached to the optic, allowing an action of the haptics to alter a shape of the optic, The shape-shifting flexible optic has a diameter of ≤8 mm. The dual mode AD-IOL, at rest, is in a fully accommodated configuration as a result of at least one of the shape memory of the haptic system and a shape-shifting capability of the flexible optic. A restraining component is sized and configured to immobilize the haptic in at least one of a flatter angle and a larger diameter in a disaccommodated configuration of the AD-IOL, when compared to the accommodated configuration. The AD-IOL is implanted into an eye of a patient. A capsular bag of the eye is allowed to fuse through the haptics. The haptics are released by making radial cuts therebetween, the radial cuts extending from edges of the eye's anterior capsule towards an equator of the eye's capsular bag for a distance defined to produce a desired amount of release in a stiffness of the eye's fibrosed capsular bag.

In one embodiment, during accommodation, the haptic arms flex closer to the axis of the AD-IOL and squeeze the optic vesicle and cause it to become more rounded, i.e., to have more convex surfaces with greater dioptric power. During disaccommodation, the same haptic arms may exert a pulling action on the optic vesicle, causing it to stretch laterally, and consequently have a less convex surface, i.e., lower dioptric power.

The optic vesicle may be manufactured from two separate components, an optic anterior capsule and an optic posterior capsule. The two are fused at their outer edges allowing the space in between to be filled with fluid. The fluid may have a higher index of refraction than water thereby conferring the biconvex optic vesicle a positive dioptric power. Ideally, the index of refraction of the fluid matched the index of refraction of the optic vesicle, thereby eliminating and optical interference from the internal surfaces of the optic vesicle.

In one embodiment, the optic vesicle is designed to be relatively small and comparable in size or volume to a standard monofocal IOL optic, with an overall disaccommodated diameter of 8 mm or less mm and optical zones of 6 mm or less, in a human sized AD-IOL. The same optic vesicle embodiment, sized for an experimental model consisting of a Rhesus monkey eyes, has an overall diameter of 6 mm and an optical zone of 4 mm.

In one embodiment, one of the optic capsules, for example the anterior capsule, has an optical zone that is thicker or more rigid such that it does not alter its shape under the forces of accommodation or disaccommodation produced in the eye. This is the prescription component of the IOL adapted to correct an individual patient refractive error. It may be shaped to confer a fixed amount of the refractive power of the IOL and also possibly an astigmatic correction power if desired. The axis of such a astigmatic correction may be marked on the edges of this thicker optical zone or structure fixing the optic.

In one embodiment the opposite capsule, for example the posterior optic capsule, remains maximally thin and flexible to allow maximum bowing or flattening under pressure or tension, from the arms of the haptic system, and thus confer an additional number of diopters during accommodation. This is the accommodative component of the optic.

In one embodiment the volume of fluid filling the optic vesicle is constant in all AD-IOLs and the curvature of the thin flexible optic zone is predictable. The variations in power required for different eyes are controlled by the fixed power of the rigid optic zone, the prescription component.

In one embodiment the optic anterior capsule and or the posterior capsule have a more rigid zone that is thicker and shaped to fit within the haptic optic ring or fusion zone or other haptic devices for secure centration. In other embodiments, ridges, protuberances or other structures ensure centration in the optic ring or other haptic devices.

In one embodiment the optic anterior or posterior capsule has a thinner, maximally flexible zone that corresponds to the haptic flexion zone, and allows a change in the shape of the optic vesicle with minimum resistance. This flexion zone is peripheral to the optic zone. In another embodiment the flexion zone has external pegs for direct attachment of haptic proximal ends.

In one embodiment the optic anterior or posterior capsule has thicker zones, blocks with grooves to incorporate and fix the haptic radial arms. Additional thicker and more rigid zone may exist in between haptics. The overall rigidity of this zone allows it to also function as a piston zone, driving fluid centrally to cause a bowing of the thinner capsule optical zones. This zone is peripheral to the flexion zone.

In one embodiment, the haptic arms have wide plate like structures adapted to press on the optic flexion zones.

In one embodiment, the outermost zone of the optic anterior capsule, on its underside, has a fusion zone designed to become fused to a corresponding zone on the posterior capsule of the optic vesicle. Channels or groves allow excess bonding material to pool at the fusion zone and not spread out. One or more fluid filling channels may be built into the thicker blocks zone or other suitable locations.

In one embodiment, columns or ridges or ribs are built internally between the anterior and posterior capsule to diminish movement of the more rigid prescription zone during accommodation. Such structure have the added benefit of adding structural stability to the shape of a flexible optic and limit distortion.

In one embodiment the optic vesicle is filled with fluid to the full non-stretch or minimally stretched volume, where the capsules of the optic vesicles are shaped set for a disaccommodated configuration. The accommodative elastic force of the AD-IOL is provided primarily by the haptic system.

In one embodiment the optic vesicle is constructed separately and independently from the haptic system and the two are assembled together by pressing the optic vesicle into the haptic structure. The optic vesicle can be snapped into and secured to the haptic system by precise geometry and mechanical snug fit, or parts of it may be incorporated into the fusion zones, or it may be additionally secured after assembly with additional polymer or adhesive added to the grooves containing haptic arms or other haptic attaching components.

In one embodiment, the haptic system is maintained disaccommodated after IOL implantation with a loop, or a ring of polypropylene or other similar biocompatible materials, that can be transacted and rendered inoperative by the use of a laser, for example a YAG or femtosecond laser, or surgical instruments. Such loop may be fixated to positions of AD-IOL, so that if the restraining loop is cut, the segments of the loop remain attached to the AD-IOL outside of the optical zone, and need not be removed from the eye.

In one embodiment the optic may incorporate an artificial iris element that blocks the passage of light through the peripheral zone of the optic from being transmitted to the inside of the eye. The peripheral zone undergoes purposeful mechanical alterations that reshape the central optical zone, but in themselves can cause undesirable image distortions and artifacts.

In one embodiment, the optic may incorporate a mechanical reinforcement element, that stabilizes the shape of the optic vesicle and may have shape memory or superelasticity.

In one embodiment, the optic vesicle may have an integrated haptic restraining component that is separate from the haptic system.

In yet another embodiment, the incorporated artificial iris, reinforcing element, and the haptic restraining element may coexist in a single element, and this element may have a non-reflective surface.

In one embodiment, the haptic system may be adapted to be rolled into a narrow cylinder to facilitate its injection into the capsular bag at the time of surgery. Such adaptations may include, but not be limited to altering the number of haptic arms, altering the connections between the haptic arms, altering the shapes or sizes of loops that allow the eye's anterior and posterior capsule to fuse through and thus fixated the haptics, and any other feature known to one of skill in the art.

In another embodiment, two or more optic rings with two haptics each are superimposed and can rotate about the optic. Before loading the AD-IOL in an injector, the top ring or rings are rotated so that their haptics overlay the bottom ring, in effect forming a two-haptic AD-IOL for the purpose of limiting injector size. Once implanted into the eye, the surgeon rotates the top ring or rings so that all four or more haptics are uniformly distributed in the capsular bag.

In certain embodiments, the optic vesicle, restraining ring, and haptics may each include a biocompatible plastic, such as polypropylene, poly(methyl methacrylate), polyamide, nylon, polyester, polyvinylidene fluoride, and/or silicone. The haptics and optic securing components and restraining components may each include a biocompatible metal or alloy, such as stainless steel and/or nickel titanium alloy.

In one embodiment, the optic vesicle is filled with a biocompatible fluid with an index of refraction greater than water, such as but not limited to silicone oil.

In another embodiment of the invention, the optic vesicle is filled to a non-stretch or minimally stretched volume and shape set for accommodated configuration. In this embodiment, the action of zonular capture haptics is primarily to stretch the optic vesicle to its disaccommodated, flatter shape. The elastic accommodative force is contained primarily in the fluid-filled vesicle, not in the haptic structure.

In this embodiment, the AD-IOL is implanted in a stretched disaccommodated configuration, by the action of a restraining device.

In another embodiment, the elastic accommodative force is contained in the shape memory of both the fluid-filled vesicle and in the haptic structure, and their elastic recoil may be additive or subtractive to result to an overall level that can be disaccommodated by zonular tension, at about 1 gram of force or less per individual haptic.

In another embodiment, the optic vesicle can alter its surface area to volume ratio as it changes from accommodated to disaccommodated state to conform to the required geometry by stretching or un-stretching the optic flexible zone or by pumping in or drawing our fluid under the action of the haptics.

BRIEF DESCRIPTION OF THE DRAWINGS

FIG. 7A depicts an assembled AD-IOL with a restraining ring above it and FIG. 7B is an exploded view of the components;

DETAILED DESCRIPTION

All patent applications, patents, and other references cited herein are hereby incorporated by reference in their entirety into the present disclosure.

In ophthalmology, the term "haptic" refers to a structure that extends out from an optic element of an intraocular lens, usually for holding the lens in place within the capsular bag of the eye. Herein, "haptics" are sometimes referred to as "zonular capture haptics," or collectively as a "zonular capture haptic system," or simply "haptic system" and refer to structures or material that not only assist with placement and centration of the lens within the capsular bag to transmit zonular movement to the lens, but also permit secure fixation in between or to the anterior or posterior capsule following removal of the natural lens and placement of the artificial lens. A haptic system may also include an optic retainer for holding an optic. An "optic retainer" is a portion of the haptic system that holds the optic, e.g., a ring, pins, or other attachment mechanism.

Figure 1A:
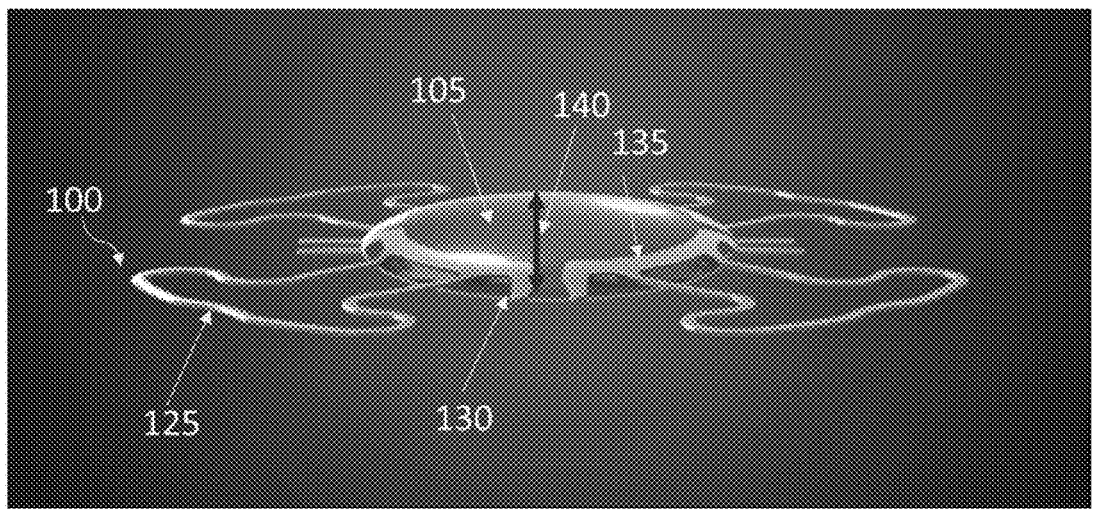
FIGS. 1A and 1B are perspective views of a dual mode AD-IOL in disaccommodated (FIG. 1A) and accommodated (FIG. 1B) positions, illustrating both the axial shift and the shape shift of the optic with accommodation, in accordance with an embodiment of the invention.
Figure 1B:
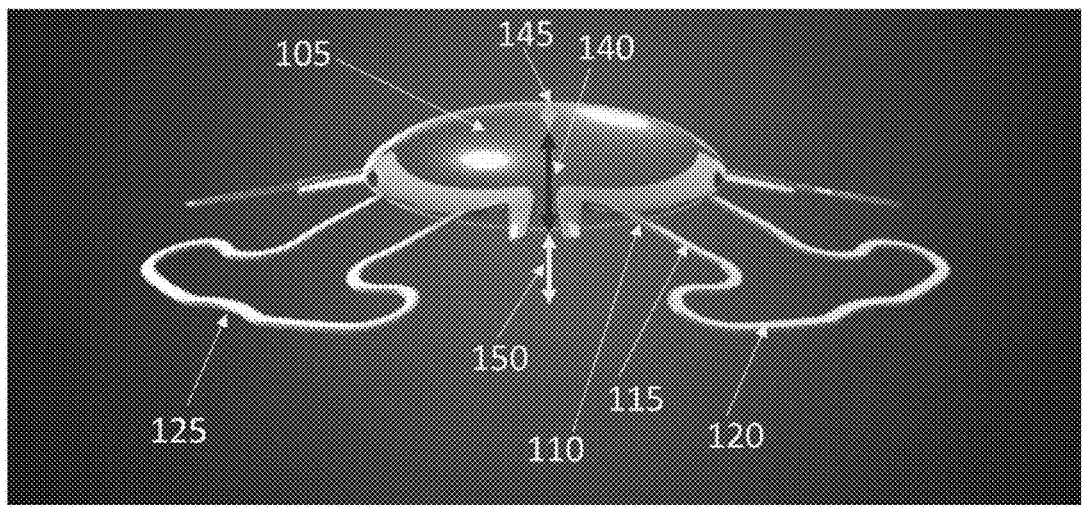

FIGS. 1A and 1B depict one embodiment of a dual mode accommodating-disaccommodating IOL with zonular capture haptics 100 coupled to a both axial and shape-shifting flexible optic 105. The zonular capture haptics 100 have been previously described in U.S. Pat. No. 9,364,318, incorporated herein by reference in its entirety. The zonular capture haptics 100 include a flexion zone 110, a radial arm 115, and a capsular bag capture zone 120 that has a sinusoidal indentation 125 that allows the circumference to change simultaneously with the equator of the capsular bag. Each individual haptic 100 has a T-shaped, closed loop configuration that allows contact and fusion of the anterior and posterior capsules of the eye through and around the closed loops. The plurality of haptics 100 defines a disc that is coexistent with the fused capsular bag. The equatorial zones of the haptics 100 are generally circumferential with the capsular bag equator and provide the main anchoring zone of the fused bag to the haptic system; hence they represent the zonular capture zone. Restraining tabs 130 protrude horizontally and radially out of the optic ring 135 between haptics 100 or, alternatively, on both sides of each haptic arm 115. They extend in length past the length of the flexion zone 110 and they are constructed to be relatively rigid in comparison to the flexion zone of the haptic arms 115. The haptics 100 are shaped set to be in an accommodated configuration at rest, and can be restrained by securing them to restraining tabs 130 into a flat disaccommodated configuration with a biocompatible suture or other similar devices. The haptics 100 are preferably constructed from nitinol, as thin as 0.001"-0.002" and can be disaccommodated by zonular tension exerted via the fused capsular bag at about 1 or less gram of force on each haptic 100.

The zonular capture haptics 100 are connected to each other and the optic 105 by an optic ring 135, which may be a single continuous structure or may be made of multiple segments or elements designed to hold the optic 105. The optic ring 135 or optic ring segments may attach to the optic 105 by a snug fit to parts of the optic 105, by being fused to the outside of the optic 105, or by being contained in part or in whole inside the fusion zone of the optic 105 or other parts of the optic 105 adapted for this purpose.

In FIG. 1A, the IOL is shown in a flattened, disaccommodated position and the disaccommodated optic thickness is highlighted by the double arrow 140. In the accommodated position in FIG. 1B, the lens thickness increases by an additional amount, depicted by the double arrow 145 and the optic shifts axially by vaulting anteriorly in the eye by an amount depicted by the double arrow 150.

In use, restraining tabs 130 are utilized to lock the haptic structure at implantation and for some weeks afterwards in a disaccommmodated configuration, until such a time that the capsular bag fusion and fibrosis has completed. The haptic arms 115 are maintained in a horizontal position by virtue of a loop of biocompatible material, such as a suture woven under haptic arms 115 and over restraining tabs 130, or a ring 155 such as the one in FIGS. 11 A and 11B. The haptics 100 allow room for radial sections in the fused capsular bag from the edge of the anterior surgical capsulotomy towards the equator of the bag. The length of these radial cuts can be adjusted to the amount of capsular bag fibrosis restriction release necessary and can be performed non-invasively with a YAG or femtosecond laser. During accommodation, the haptics 100 flex posteriorly and squeeze the optic vesicle into a more spherical shape. During the disaccommodation, they stretch it to a less spherical shape.

Figure 2:
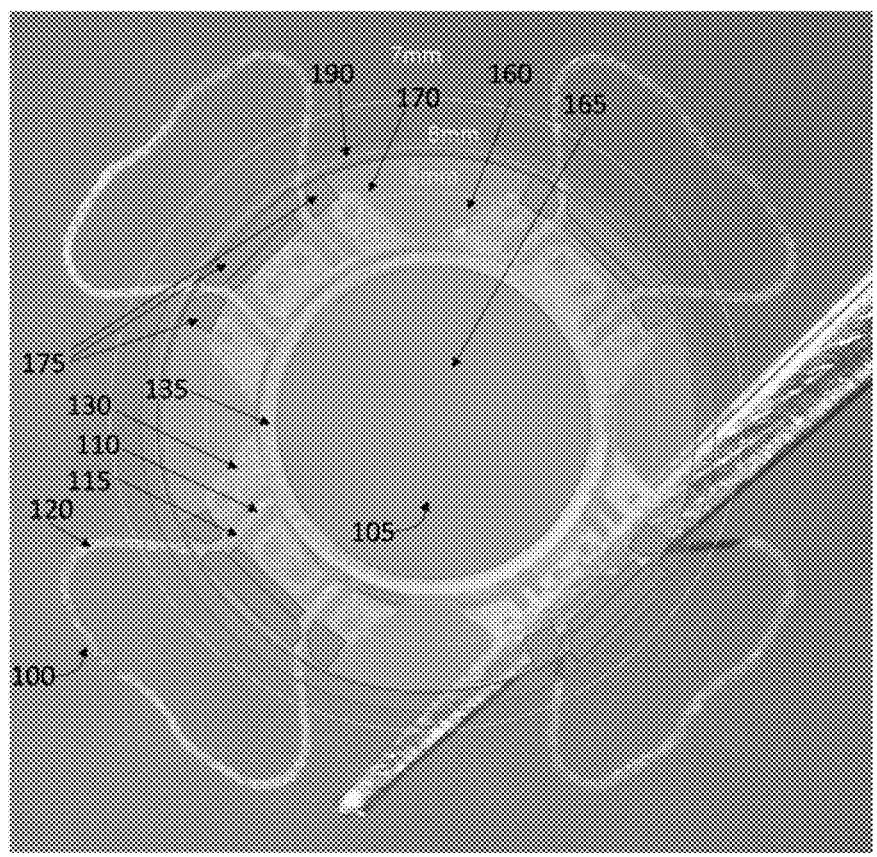
FIG. 2 is a schematic diagram of a top view of an optic vesicle in accordance with an embodiment of the invention superimposed on a photograph of a prior art haptic system, maintained in fully disaccommodated position by a surgical forceps, constructed out of nitinol and sized for a Rhesus monkey eye.

Referring to FIG. 2, the shape shifting optic 105 includes a fluid-filled vesicle. The optic vesicle is depicted superimposed on a photograph of a haptic system in accordance with the prior art, to illustrate the relationship between the two structures. Both are sized for a Rhesus monkey eye. The haptic system, constructed out of nitinol is maintained in a fully disaccommodated position by a surgical forceps. The optic 100 has a thinner flexion zone 160, generally situated under the haptic flexion zone 110 and peripheral to the central optic zone 165. The peripheral part 170 of the flexion zone 110 may be thicker and function as a piston zone; the peripheral part 170 may have more rigid components, shaped as blocks 175 to retain and fix the distal part of the haptic arms 115.

Figure 3A:
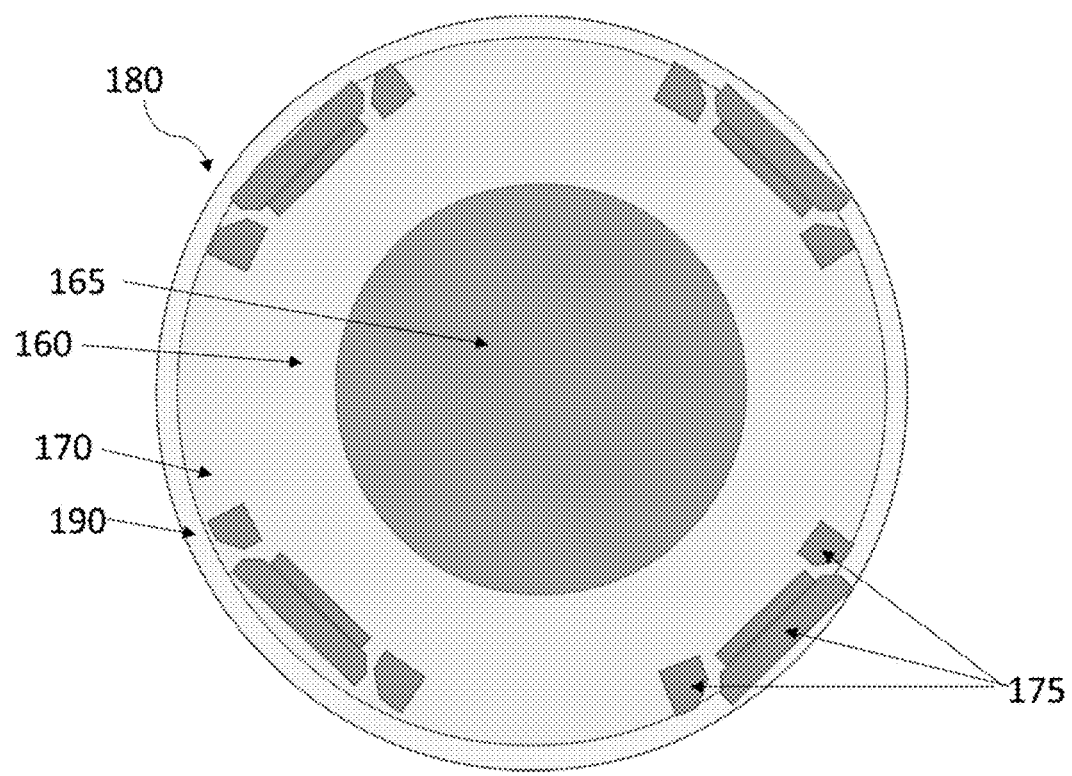
FIGS. 3A, 3B, 3C, and 3D are schematic diagrams of optic anterior and posterior capsules, specifically anterior top view (FIG. 3A), cross-section (FIG. 3B), posterior from above (FIG. 3C), and in cross-section (FIG. 3D), in accordance with an embodiment of the invention.
Figure 3B:
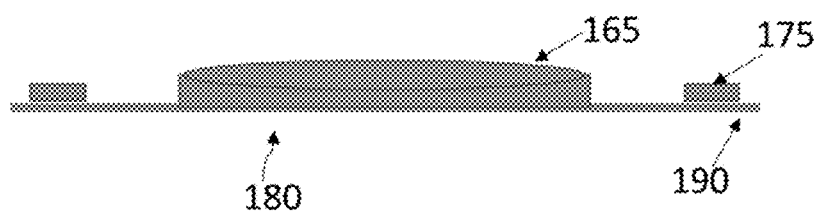
Figure 3C:
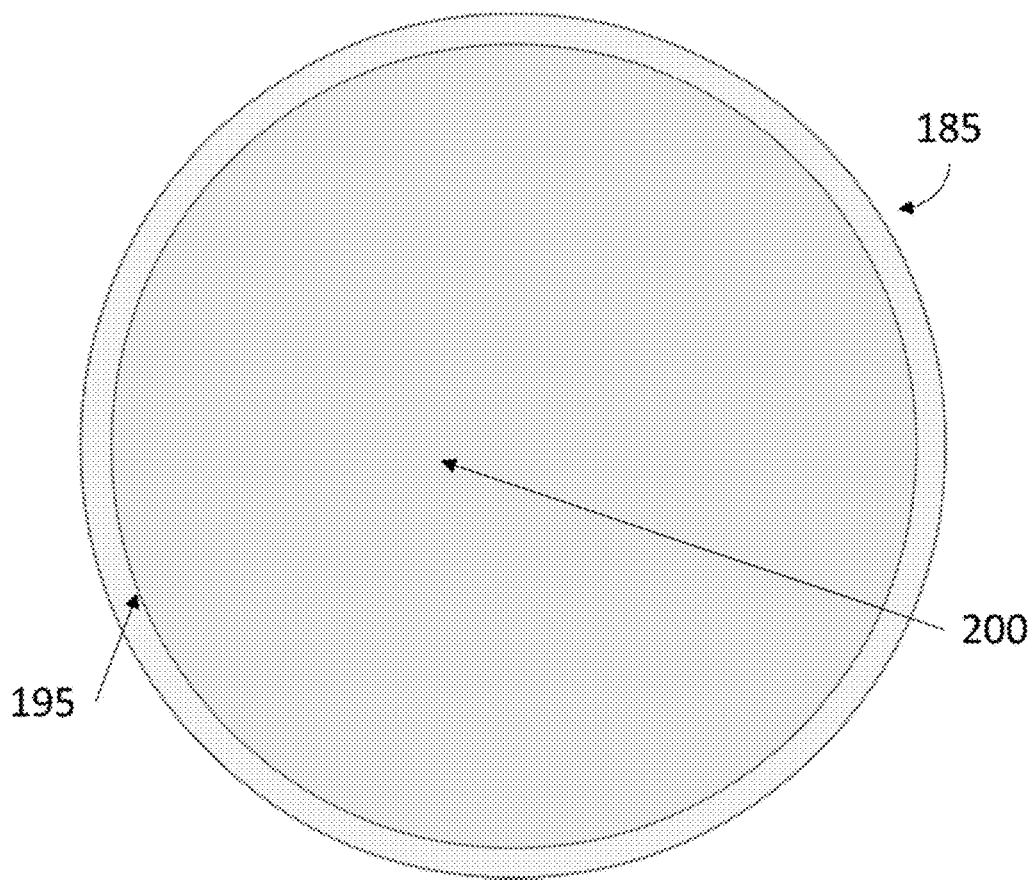
Figure 3D:
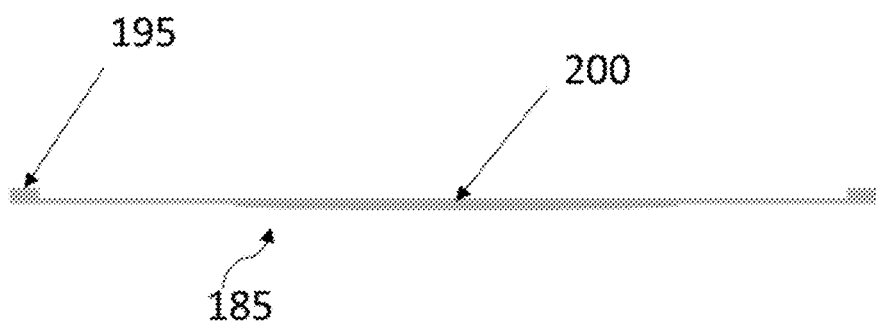

FIGS. 3A, 3B, 3C, and 3D are diagrams of the components of the shape shifting optic 105 shown in FIG. 2, specifically anterior top view (FIG. 3A) and cross-section (FIG. 3B), posterior from above (FIG. 3C), and in cross-section (FIG. 3D). The optic has an optic anterior capsule 180 and an optic posterior capsule 185.

In one embodiment the optic anterior capsule 180 has a central optical zone 165 that is thicker, more rigid and fits snugly inside of the optic ring of the haptic structure. Such optical surface may provide a predetermined customizable power for the IOL that is specific for each patient, for example 15 D vs. 16.5 diopters, and may have an astigmatic correction component as well, if so desired. This is the prescription component of the IOL. The axis of this surface is marked on the edges of the optic zone or the haptic structures holding the optic 105 in place. In one iteration, the greater thickness of the fixed optical surface, for example 200-500 microns, is elected to make it sufficiently rigid as to not be altered in the shape by the actions of the haptics 100 or shifting fluid. Immediately peripheral to the optical zone 165, a thinner flexion zone 160, generally situated under the haptic flexion zone 110, facilitates a shape change for the optic 105 under the squeezing or pulling effect of the radial haptic arms 115 during accommodation. The flexion zone 160 may be as thin as 25-50 microns. The peripheral aspect of the flexion zone 160 may be more rigid 170 and function as a piston zone and has more rigid components, shaped as blocks 175 to retain and fix the distal part of the haptic arms 115. The haptic arms 115 may fit snugly, e.g., snap in, in the grooves or notches within or in between these blocks and may be additionally secured with a biocompatible polymer or adhesive when the lens is assembled. The outermost edge of the optic anterior capsule, on the underside of the structure, is designed as a fusion zone 190 to the corresponding fusion zone of the optic posterior capsule 195.

In addition to securing the optic to the haptic radial arms, so that the optic vesicle can be both compressed and stretched by the flexion and extension of the haptic arms, such rigid sections also function as piston zones, forcing the fluid displaced by compression during accommodation toward the center of the optic vesicle. Additional piston zones may be placed between haptics as needed.

In one embodiment, the optic posterior capsule 185 is thin, e.g., having a thickness of 25 microns to 50 microns for example, and fused on its outer most edge 195 to the optic anterior capsule. The central portion of the optic posterior capsule is the optical zone 200 and may or may not have an additional molded refractive shape and it represents a variable power optical zone, the accommodating component of the IOL.

Figure 4:
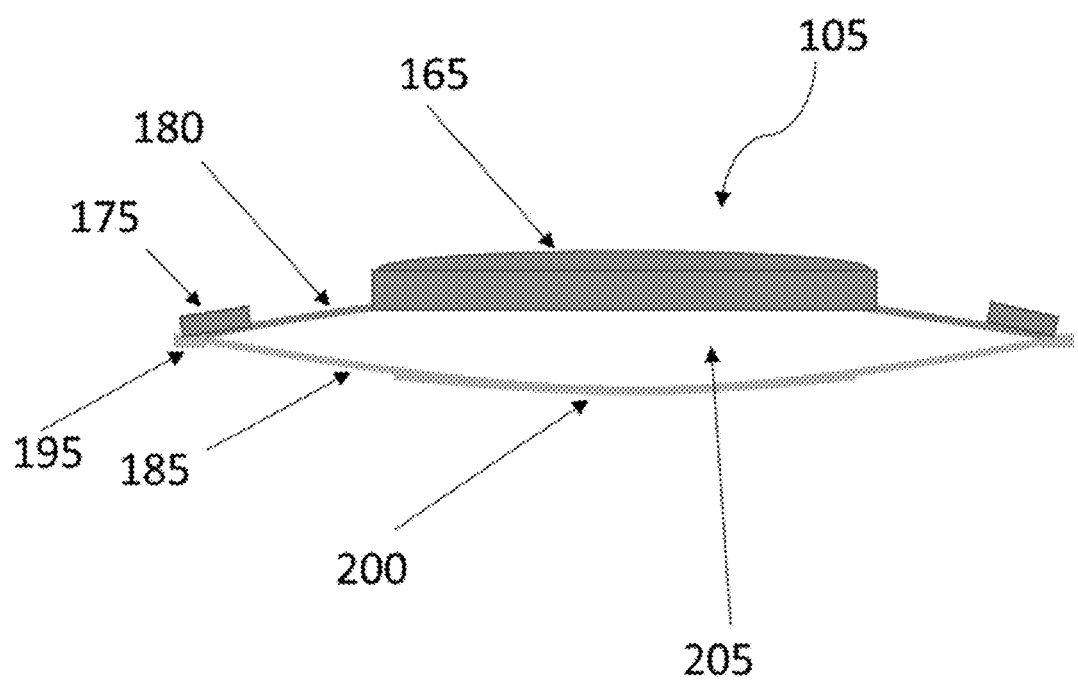
FIG. 4 is a schematic view of optic anterior and posterior capsules in cross-section, after having been fused and the optic vesicle has been filled with fluid in accordance with an embodiment of the invention.

Referring to FIG. 4, the components illustrated in FIGS. 3A-3D may be assembled to form a shape-shifting optic 105. A space 205 between the anterior and posterior capsules is filled by a biocompatible fluid with an index of refraction higher than that of water, such as, for example, silicone oil. Ideally, the fluid has the same index of refraction as the material in the optic vesicle, thereby reducing any internal optical interferences. When the optic vesicle is filled with fluid, the thin posterior capsule assumes a convex configuration, creating a positive refractive surface.

During accommodation, when the haptic arms 115 flex toward the axis of the IOL, fluid in the optic 105 is displaced centrally by the piston zones of the optic anterior capsule, resulting in additional bowing of the optic posterior capsule and an increase in its refractive power. The optic posterior capsule in this embodiment is sufficiently thin to undergo shape shifting with minimal resistance to the haptic arms 115. In another embodiment, the thicker, fixed optical zone may be placed on the optic posterior capsule and the variable optical zone on the optic anterior capsule. In such an embodiment, additional pegs or ridges or other fixation structure (not shown) may be built on the optic anterior capsule to allow its centration on the haptic optic ring 135.

In another embodiment, the entire optic 110 is manufactured in a rotational mold machine that creates a single vesicle at once and eliminates the need to fuse separately molded capsules.

Figure 5A:
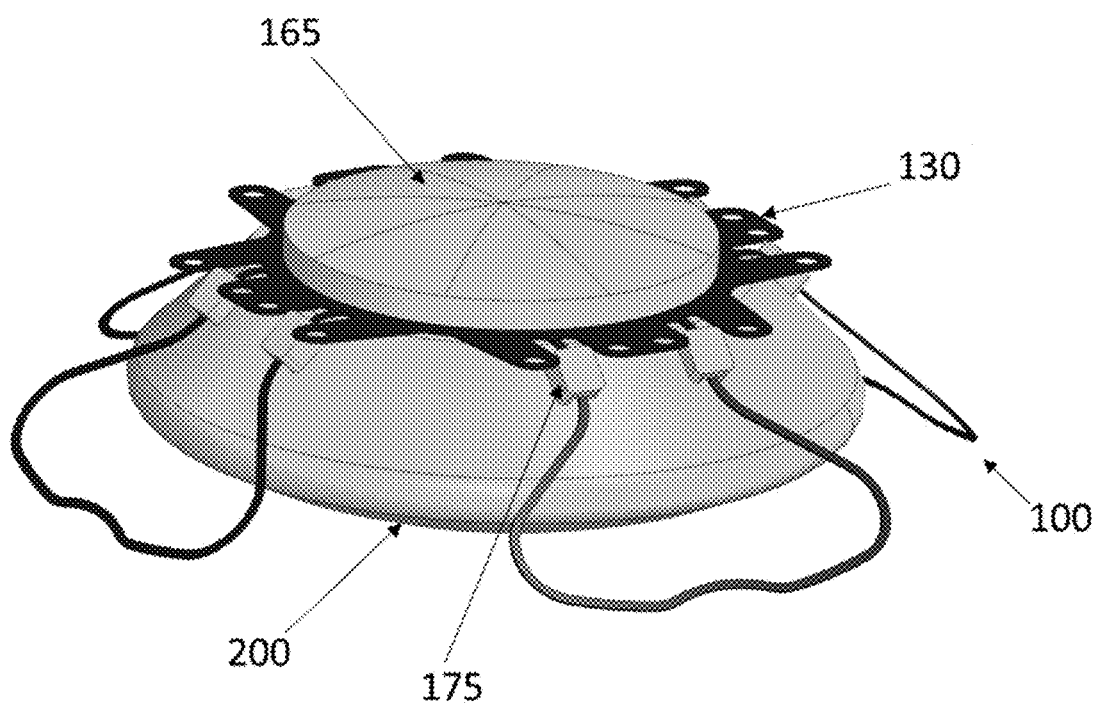
FIGS. 5A and 5B are CAD-generated images of a fully assembled dual mode AD-IOL in a perspective view (FIG. 5A) and in partial cross-section (FIG. 5B), revealing the interaction of the optic vesicle with the haptic system, in accordance with an embodiment of the invention.
Figure 5B:
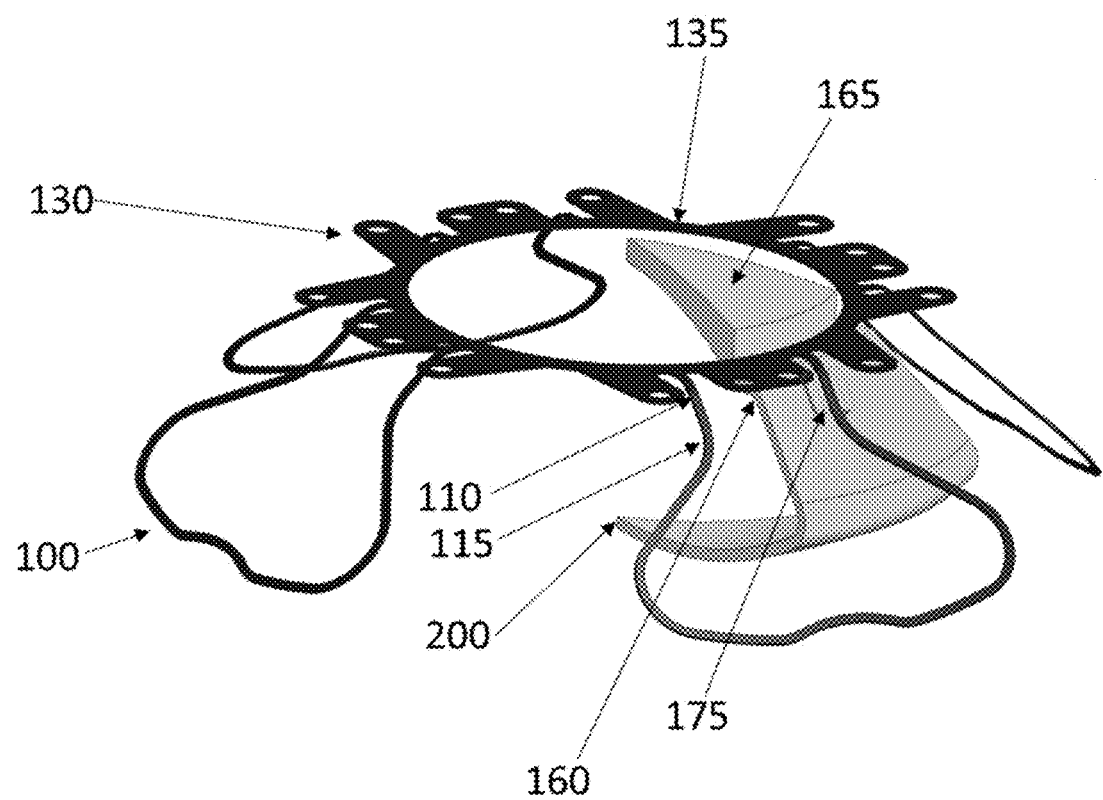

Referring to FIGS. 5A and 5B, an exemplary combination of a haptic system with an optic vesicle is illustrated. The CAD generated images show a perspective view (5A) and cross-section (5B) of a dual mode AD-IOL with the prescription component on the rigid anterior capsule 165 and the variable accommodating component on the thin posterior capsule 200; the relationship between the haptic flexion zones 110 and the optic flexion zones 160 is illustrated as well. The flexion of the haptics 110 during accommodation drives fluid centrally to force the accommodative component to become more spherical. The extension of the haptics 100 during disaccommodation drives fluid peripherally to cause the accommodating component to become less spherical. The shape memory of the optic 105 and the haptic systems is configured to provide, in sum, an accommodative elastic force smaller than the disaccommodating force generated by the eye, so that the movement of the AD-IOL can be controlled by the action of the ciliary muscle. For example, the haptic system may be shape set for an accommodated configuration while the optic 105 is shape set for a disaccommodated configuration, or vice versa, or both the haptic system and optic 105 may be set for accommodated configuration. The exact combination is determined by the dimensions and the material properties of the haptic and optic systems.

Figure 6A:
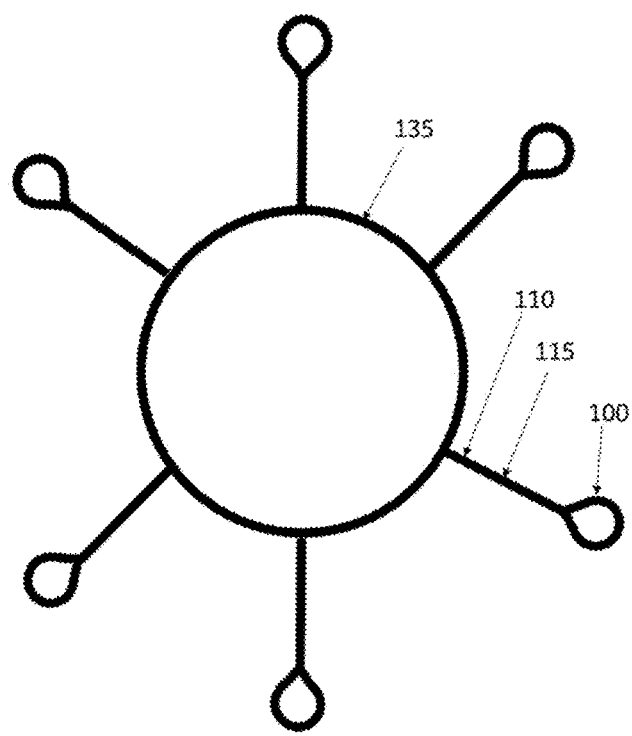
FIG. 6A is a schematic view of a haptic structure in accordance with an embodiment of the invention, including some modifications to allow rolling of the AD-IOL into a tight cylinder, to facilitate implantation by injection into the eye through a small incision.

Referring to FIG. 6A, in one embodiment, the haptic system may be adapted to be rolled into a narrow cylinder to facilitate its injection into the capsular bag at the time of surgery. Such adaptations may include, but not be limited to altering the optic ring 135, the flexion zones 110, and/or the number of haptic arms 115, altering the connections between the haptic arms 115, altering the shapes or sizes of loops of haptics 100 that allow the eye's anterior and posterior capsules to fuse through and thus fixate the haptics 100, and any other suitable feature known to one of skill in the art. In the illustrated embodiment, the closed loops of the haptics 100 at the end of each haptic arm 115 have a reduced diameter proportionate in size to the inner diameter of the injection tube, so that they can pass through the tube without being crimped into a permanently distorted shape. For the same reasons, the haptics arms 115 are narrow and oriented such so that they can be rolled over the optic 105 into the injection tube along the 6-12 o'clock axis, for example. Rolling the haptic arms 115 over the rolled optic 105 prevents a sharp bend in the material that may lead to crimping or permanent disfiguration of the haptics 100.

Figure 6B:
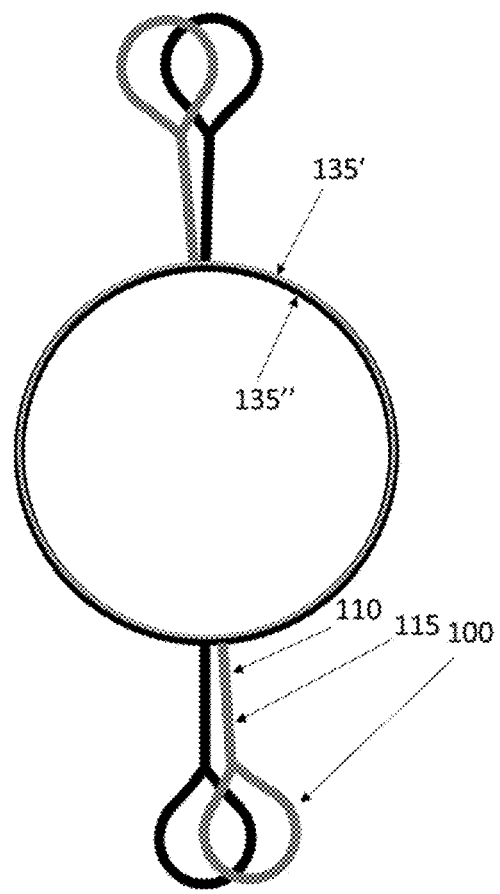
FIGS. 6B and 6C show an embodiment of the invention in which two optic rings with two haptics are overlaid and can rotate about the optic, so that prior to loading in the injector, the top ring is rotated with its haptics overlaying the haptics of the bottom ring. Once implanted in the eye, the surgeon rotates the top optic ring by 90 degrees, restoring the four-haptic configuration.
Figure 6C:
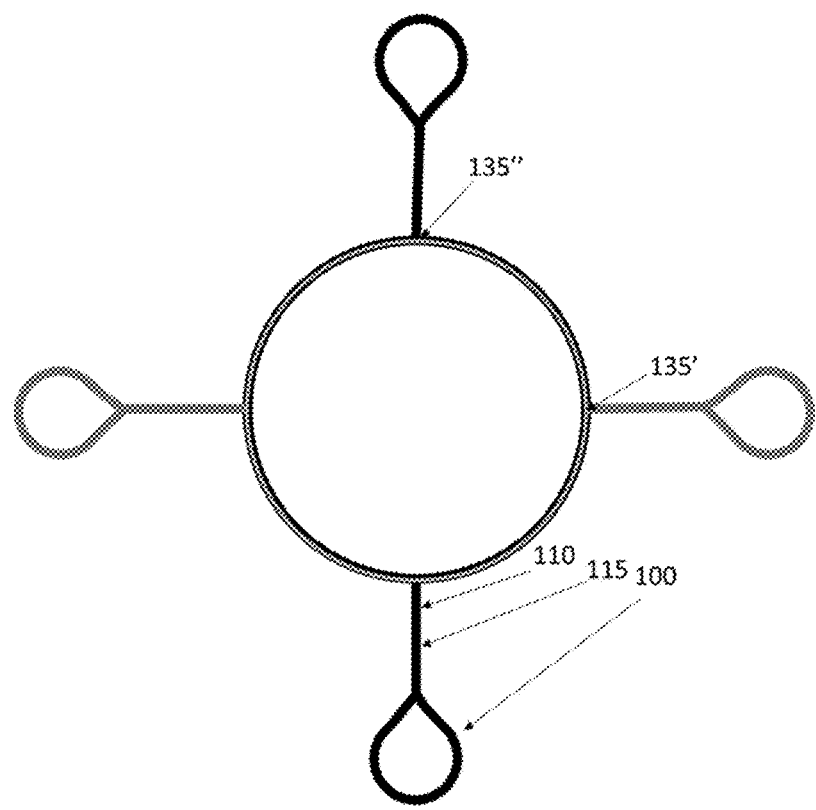

FIGS. 6B and 6C show an embodiment where two optic rings 135' and 135", having two haptics 100 each, are overlaid and can rotate about the optic 105. Prior to loading in the injector, the top optic ring 135' is rotated with its haptic arms 115 overlaying the haptic arms 115 of the bottom optic ring 135", in effect presenting only two haptics 100, 180 degrees apart, to the injector. Once implanted in the eye, the surgeon may rotate the top optic ring 135' by 90 degrees, restoring the four-haptic configuration. Alternatively, multiple optic rings 135 can be overlaid for haptic configurations with more than four haptics 100. The greater the number of haptics 100, the more uniform is the transmission of zonular forces to the optic 105 and the better the control the capsular bag geometry through the fibrosing phase but the complexity of the design of the IOL and the injector is greater and the implantation is more difficult. The minimum number of haptics 100 to achieve the right balance, possibly three to four, can only be determined by the specific materials and dimensions used for any iteration. The bottom optic ring 135" contains the diasaccommodative restraining device (not shown). In FIG. 6A the haptics 100 are nearly completely overlapped, in FIG. 6B they are in the desired configuration.

In one embodiment, the volume of fluid inside the IOL is calculated to be constant fill, to a non-stretch or minimally stretched vesicle volume. This allows shape shifting of the vesicle with minimal resistance. The fill of the optic vesicle bows out the variable power zone, the accommodating component, on the optic posterior capsule, for example, to a predetermined and fixed power for each corresponding haptic configuration. This power added to the power of the rigid optical zone, the prescription component, on the opposite capsule constitutes the IOL power for that particular haptic configuration, for distance or disaccommodated vision. Additional power is obtained during accommodation by the compression caused by the flexion of the haptics 100, elastic recoil of the optic vesicle, or both, which bows the optic posterior capsule further and, in doing so, increasing its power by up to 14 diopters. One or more filling channels can be constructed within the thicker regions of the optic vesicle such as the pistons blocks or haptic retaining blocs, or any other suitable locations. These channels are utilized to fill the optic vesicle with fluid and remove any inadvertent air bubbles during assembly.

Figure 7A:
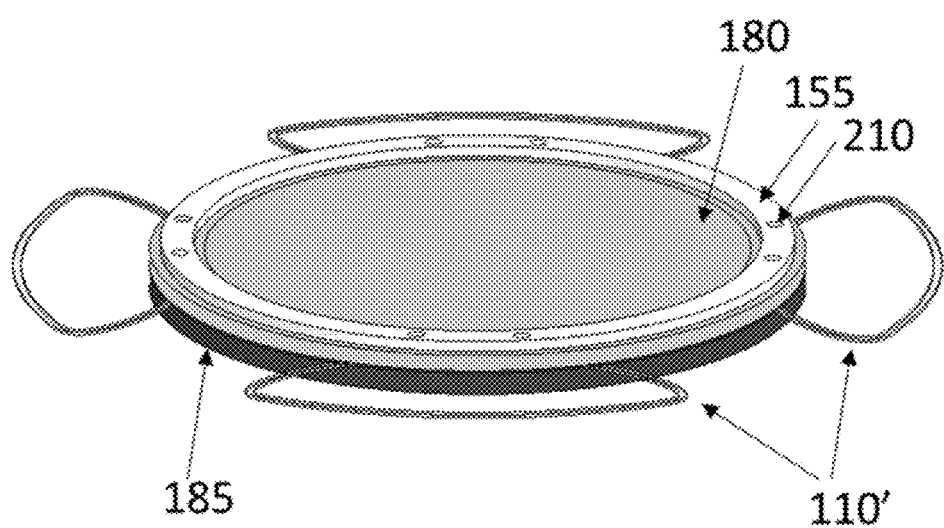
FIGS. 7A and 7B are CAD-generated images of an optic vesicle shaped and filled to the accommodated fill volume, the zonular capture haptics being independent of each other and function primarily by stretching the optic vesicle during disaccommodation, in accordance with embodiments of the invention.
Figure 7B:
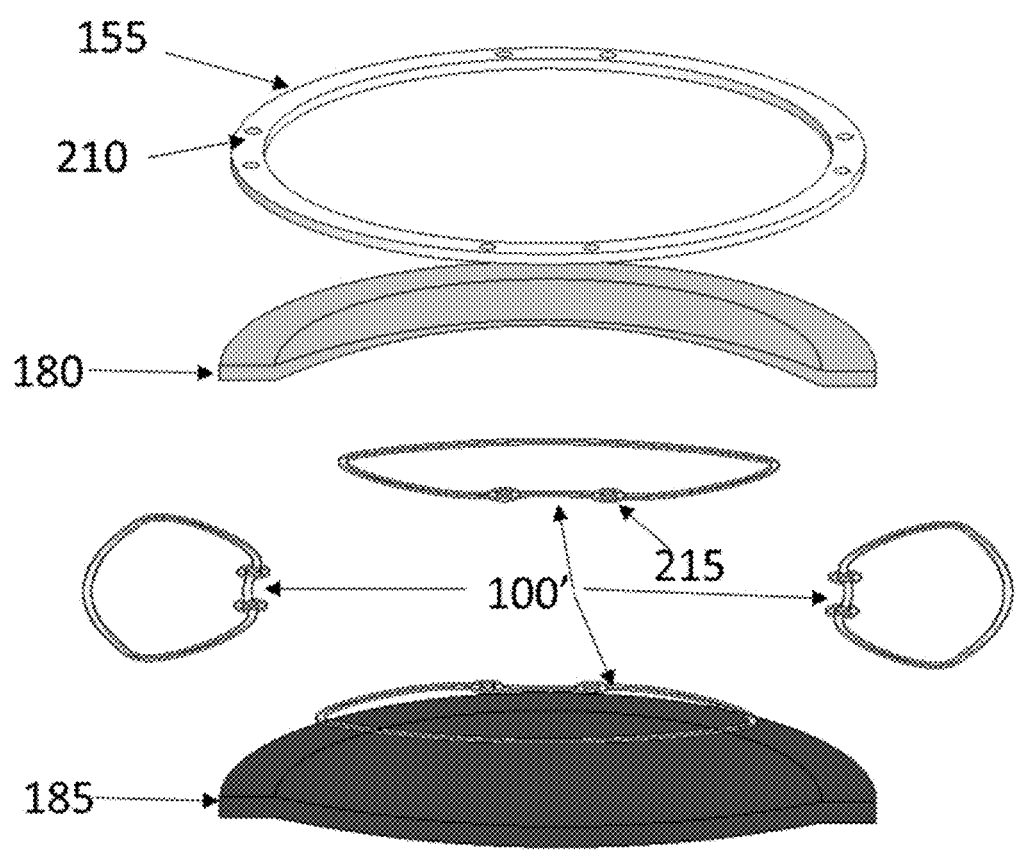
Figure 8A:
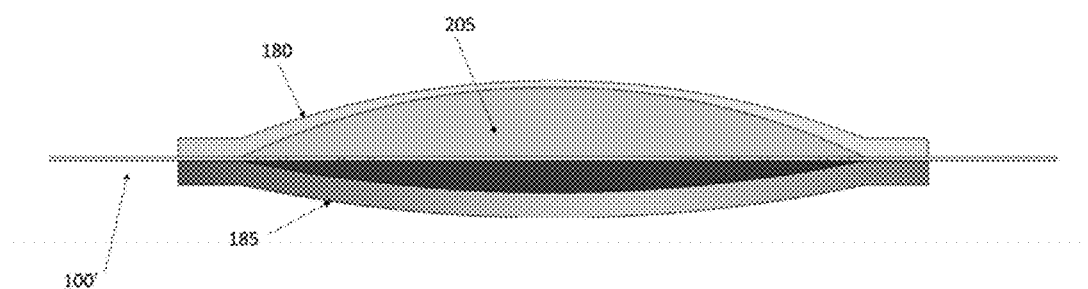
FIGS. 8A and 8B show the AD-IOL of FIGS. 7A and 7B in cross-section, in the shifted disaccommodated position (FIG. 8A) and in resting accommodated configuration (FIG. 8B). The AD-IOL has a larger diameter, and a thinner and less curved optic vesicle in the disaccommodated position.
Figure 8B:
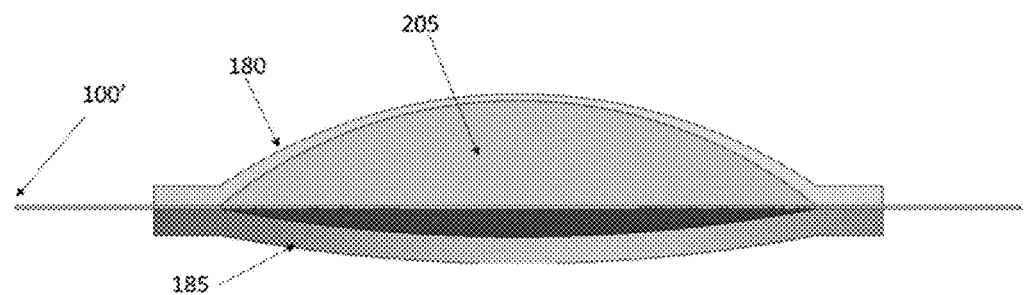

Referring to FIGS. 7A, 7B, 8A, and 8B, in another embodiment, the elastic optic vesicle is shape set for an accommodated configuration at rest. In FIG. 7A the device is assembled, including a restraining ring 155, with FIG. 7B being an exploded view with individual components. The same device is shown in cross-section in shifted disaccommodated configuration (FIG. 8A) and resting accommodated configuration (FIG. 8B). In these instance, the haptics 100 act by stretching the optic in disaccommodation.

Figure 9:
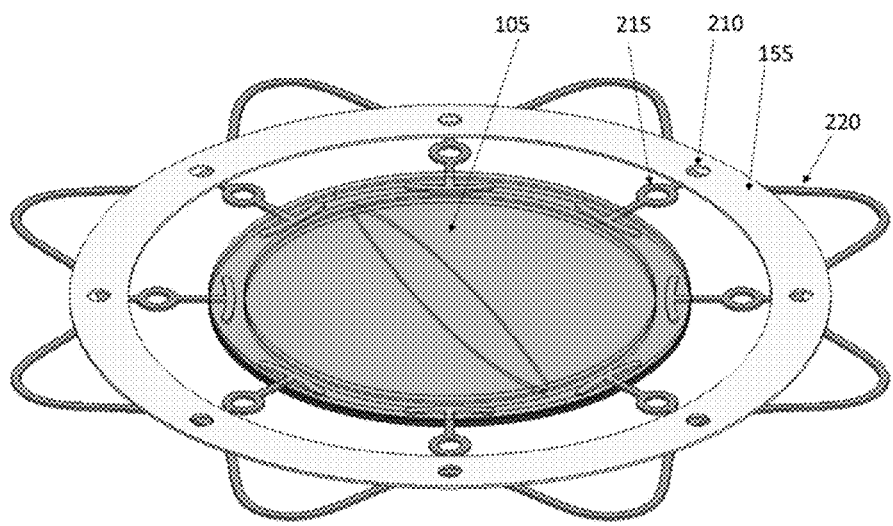
FIG. 9 illustrates an AD-IOL similar to the AD-IOL of FIG. 7, but with the haptics connected by a continuous ring, adapted to respond to a reduction in the diameter of the eye's capsular bag during accommodation, in accordance with an embodiment of the invention. In this embodiment, both the haptic structure and the optic vesicle contribute to the elastic force needed to accommodate the AD-IOL.
Figure 10:
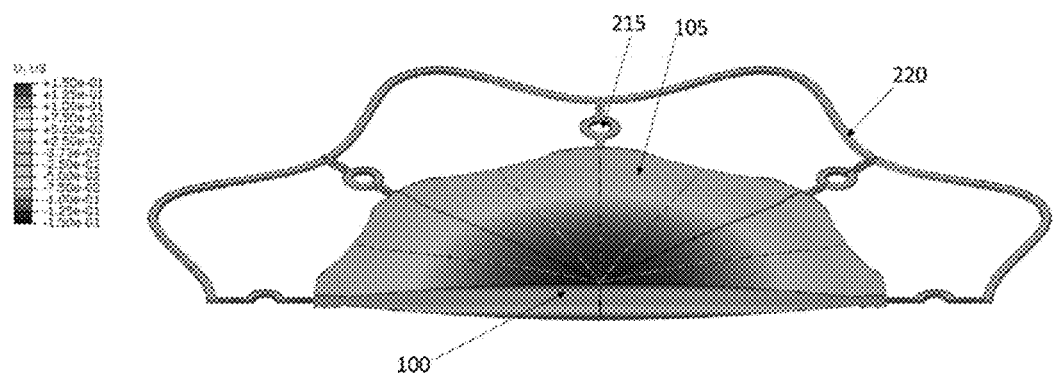
FIG. 10 illustrates a finite element analysis of the optic properties of the AD-IOL depicted in FIG. 9, showing an aberration-free optical zone in the center of the optic vesicle.

The zonular capture haptics 100' may be separate as in FIGS. 7A, 7B, 8A, and 8B. Referring to FIGS. 9 and 10, alternatively, the zonular capture haptics may be in the form of a continuous ring 220. The haptics are embedded in the fusion zone between the anterior and posterior capsules. The haptics are able to receive a restraining device in openings or notches 215. In FIGS. 7A, 7B, 8A, and 8B, the haptic segments trapped within the fusion zone define, for example, two rings each. The openings inside these rings represent restraining holes 215 and generally match in size the corresponding restraining holes 210 in the restraining ring 155. These holes may be, for example, 100-500 microns in diameter, and may be covered on both sides by the silicone layer of the fusion zone, or the opening may extend through the entire fusion zone. The exact number and dimensions of the restraining holes is determined by mechanical and thermal properties of the restraining sutures or pegs and the mechanical load exerted on them. The smaller the number and dimensions of the sutures or pegs, the safer and easier it is to release them with an external laser, provided that the restraining is stable, reliable through implantation and after, and the geometry of the locked AD-IOL is adequate.

Referring to FIGS. 7A, 7B, 11A, and 11B, the IOL may be implanted with a restraining device 155 such as a ring that has corresponding restraining holes 210 or pegs adapted to couple with the haptic restraining holes 215 to keep the optic 105 stretched or shape-shifted to the fully disaccommodated diameter. The corresponding restraining holes in the optic 105 are affixed to the holes 210 in the restraining ring 155 by a suture or a peg of biocompatible material that can preferably be cut or melted or reduced in size to break the bond, by external laser application, or with surgical instruments. The stretch of the elastic optic vesicle resists deformation during disaccommodation and returns the optic vesicle to the less stretched configuration when haptics 100 stop pulling on it. Both anterior and posterior optical zones are variable but their thickness profiles may or may not be symmetrical or uniform. The sum of their refractive powers in a disaccommodated state constitutes the prescription power, while the sum of their powers in an accommodated state represents the near vision correction for the patient. The uniform distribution of the multitude of haptics attachment points about the optic allows uniform distribution of forces on the optic 105 and leads to a distortion free optical zone, zone as seen in the Finite Element Analysis software generated diagram in FIG. 10. If a continuous haptic 220 is used, this further diminishes the risk that irregular contraction of the capsular bag may cause irregular optic distortion. The continuous haptic 220 is generally sinusoidal shaped to allow for a change in diameter in sync with the change in diameter of the fused capsular bag. A continuous haptic 220 may be shape set to contribute to either the accommodative or disaccommodative effort by a variance of its overall diameter, variance of an axial shift, or both.

After implantation, the ring 155 may be deactivated by cutting it in sections with an external, non-invasive laser or with surgical instruments, or disconnecting it from the IOL, and it may or may not need to be removed from the eye, based on multiple possible configurations.

Figure 11A:
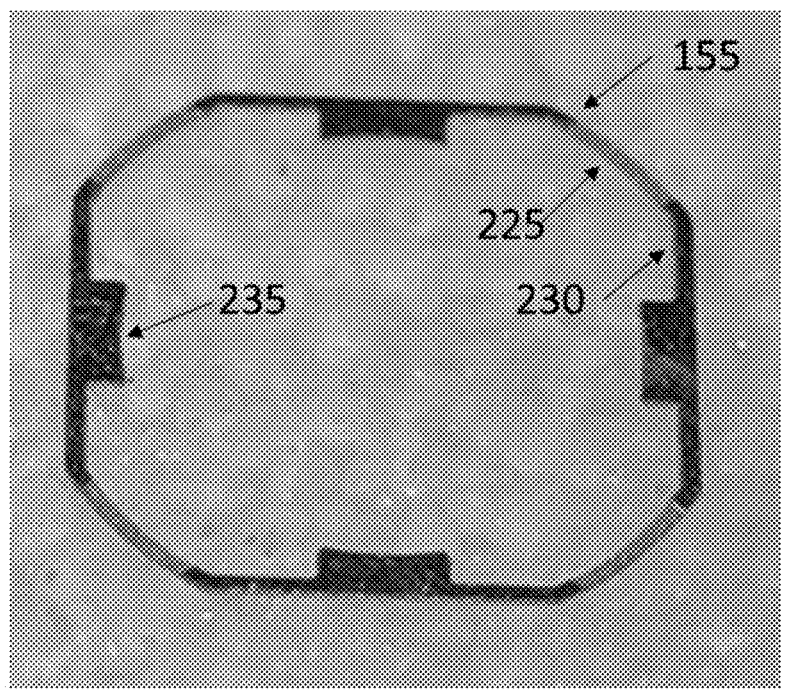
FIGS. 11A and 11B are photographs of a nitinol restraining ring (FIG. 11A), and the nitinol restraining ring in position disaccommodating the AD-IOL (FIG. 11B), in accordance with embodiments of the invention.
Figure 11B:
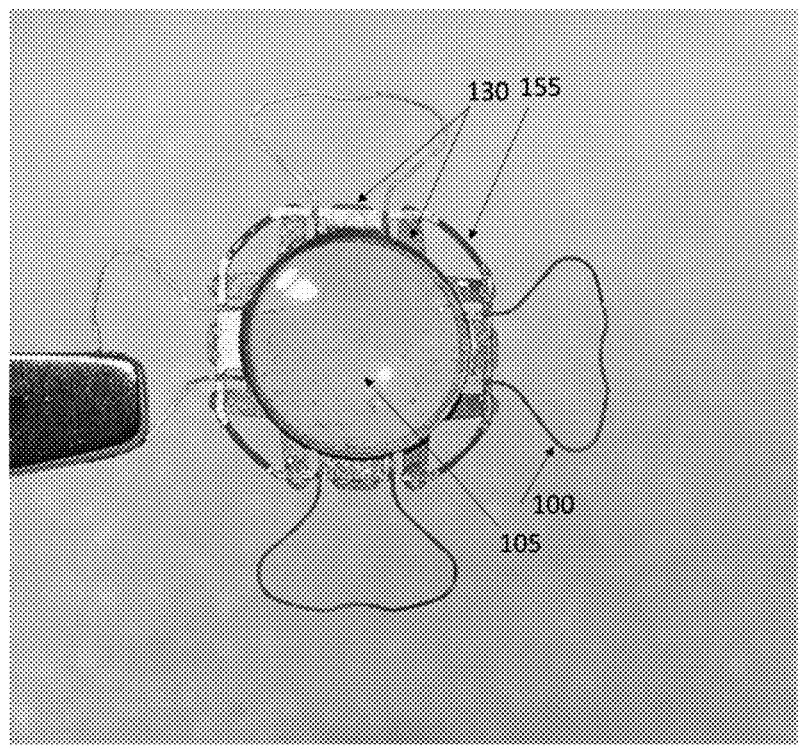

The restraining ring 155 may, as seen in FIGS. 11A and 11B, have thinner zones 225 to facilitate cutting the ring 155, thicker zones 230 to optimize the restrained position of the haptics 100, and tabs 235 to facilitate its centration. The restraining ring 155 may rest passively on the AD-IOL, or may be fixed in place.

The restraining ring may 155 be cut simultaneously with radial cuts in the fused capsular bag of the eye, between haptic elements. Such cuts may extend from the edge of the anterior capsulotomy surgically performed in the eye's anterior capsule at the time of surgical implantation, towards the equator of the eye's capsular bag, for a predetermined distance measured to cause a sufficient release in the stiffness of the eye's fibrosed capsular bag to obtain the desired amount of movement of the AD-IOL of embodiments of the invention.

Figure 12A:
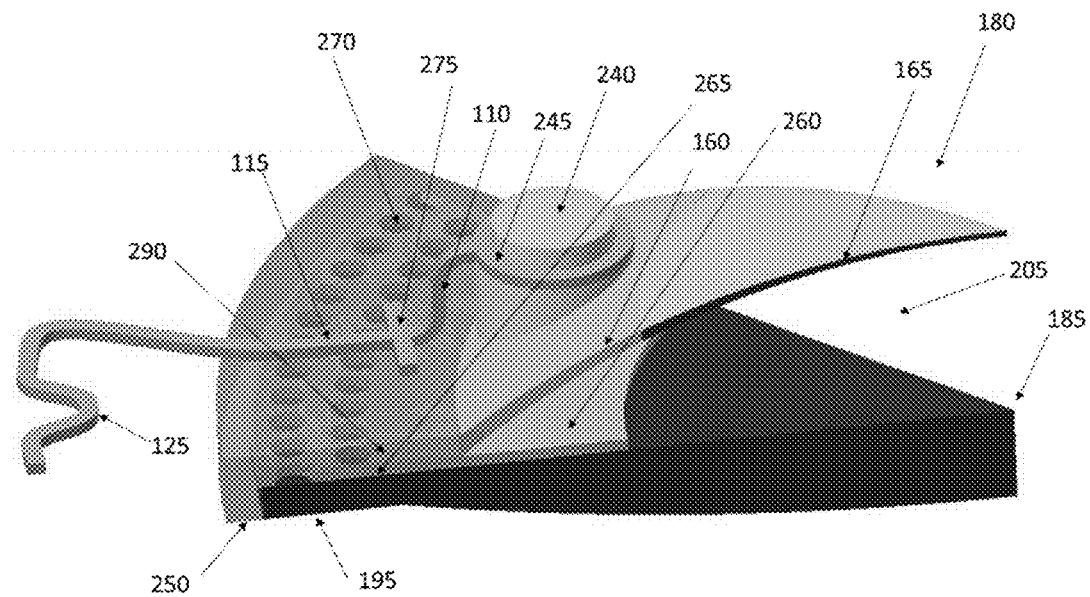
FIGS. 12A, 12B, and 12C are CAD-generated images of a section of a dual mode AD-IOL in accordance with an embodiment of the invention, in a perspective view (FIG. 12A) cross-section view (FIG. 12B), and perspective view of the entire AD-IOL (FIG. 12C). In this embodiment, the haptics exert radial pull directly on the thin anterior capsule of the optic, which represents the accommodating component of the optic. The posterior capsule is rigid and conveys the prescription optical power.
Figure 12B:
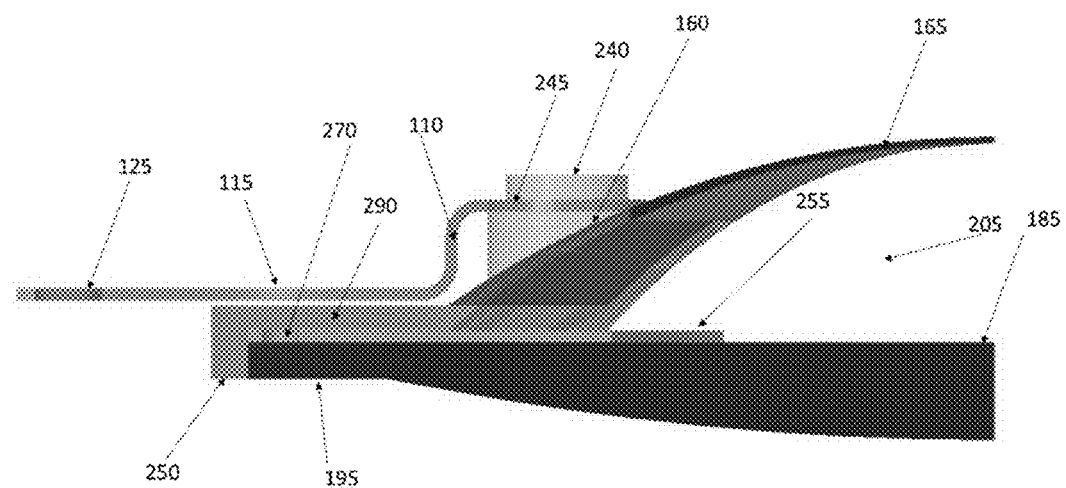
Figure 12C:
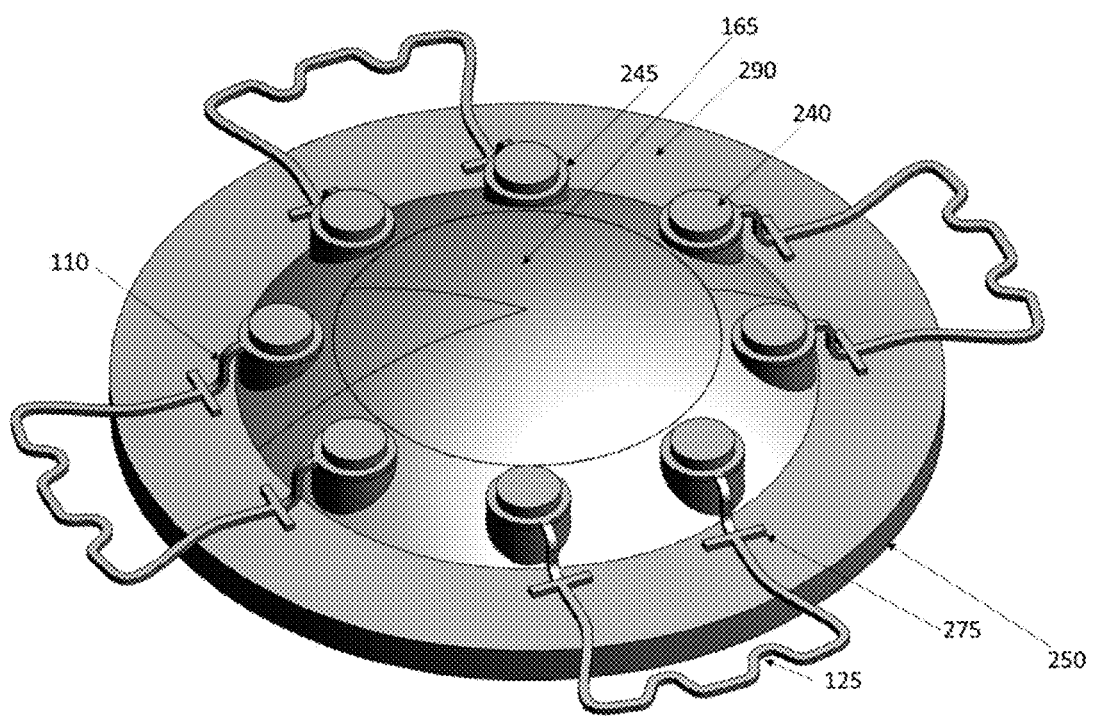

FIGS. 12A and 12B show perspective and cross-sectional CAD-generated views of a section of a dual mode AD-IOL, and FIG. 12C shows the entire dual mode AD-IOL in perspective view. In this illustrated embodiment, the accommodative component is made of a very thin anterior capsule 180 that can be as thin as 25-50 microns and built of shape memory silicone elastomer. The anterior capsule 180 may have a total diameter selected from a range of 6 to 8 mm, when in a disaccommodated position. A central optical zone 165 of the anterior capsule 180 may have a diameter selected from a range of 4 to 6 mm. Ideally the design aims for the largest optical zone afforded by the smallest diameter of the entire optic 105.

Immediately peripheral to the central optical zone 165 of the anterior capsule 180 is a flexion zone 160 of the optic 105, which includes protruding pegs 240 for attachment to haptic attachment rings 245 (described below). The pegs 240 may be circular or non-circular in shape, may protrude at a direction parallel to the visual axis, or a different direction, may have a wider base to support the haptic attachment rings, and may have a wider mushroom like cap to prevent the pegs 240 from being dislodged under tension. In an embodiment, the pegs 240 are cylindrical with a diameter of 100-500 microns and a height of 200-500 microns, with one peg 240 per haptic attachment point, preferably 6 pegs or more, preferably 8. The overall number and dimensions of the restraining pegs 240 are governed by the mechanical properties and dimension of the optic and haptic components balanced against design and usage limitations. The greater the number of pegs 240, the more uniform the zonular tension that is applied to the optic 105, the lower the mechanical load on each peg 240, and the greater the complexity of the AD-IOL construction and usage. Alternatively, the geometry of the connection between the proximal end of the haptic 100 and the flexible optic 105 may have an alternative geometry, such as a T or anchor-shaped haptic end in a matching groove, or other configurations known in the art.

The region of the flexion zone 160 between pegs 240 may be thicker and may be sinusoidal in configuration, continuously or in separate segments, to distribute the pulling vectors on the optical zone more uniformly and over a broader zone of the optical zone, without hindering the ability of the flexion 160 and optical zone to expand to a wider diameter during disaccommodation. In an exemplary embodiment, the flexion zone 160 may have a thickness selected from a range of 25 to 50 microns, and a width selected from a range of 200 to 500 microns.

Peripheral to the flexion zone 160 is a fusion zone 290 of the anterior optic, where the anterior optic is fused to a fusion zone 195 of the posterior optic 185. The fusion zone 290 of the anterior optic may have a width selected from a range of 100 to 1000 microns. An overhanging lip 250 disposed on the outer periphery of the anterior optic fusion zone, or alternatively on the posterior one, allows for better centration and a more secure seal when the elements are assembled. This anterior optic component provides the presbyopic correction.

The posterior optic element 185 is substantially thicker, to resist distortion, and carries the prescription refractive power, the power that corrects the individual patient's aphakic refraction. A thickness of the posterior optic element 185 may be selected from a range of 100 to 500 microns. The posterior optic element 195 has a posterior optic fusion zone, with a width selected from a range of 100 to 1000 microns. Generally the smallest dimension that allows the prescription optical zone to resist flexion during accommodation is preferable, as it reduces the overall bulk of the AD-IOL.

A ring-shaped plate 255 made of shape memory metal, such as nitinol, is embedded between the anterior and posterior optic fusion zones. The plate 255 extends from the outer edge of the optical zone towards to periphery and up to the overhanging lip in the fusion zone, being completely enclosed within the fused silicone capsules. The area of the plate 255 under the flexion zone 160 is solid, while the area within the fusion zone 290 is perforated by one or more concentric rings of holes, with each having a diameter of, e.g., 100 to 500 microns. The holes are preferably spaced 50 to 200 microns apart, to facilitate the use of a suture, as described below. The plate 255 may be 0.001 to 0.002" in thickness. The surface of the plate 255 may be treated to be dark, or non-reflective, by means of laser surface modification, or chemical or pigment deposition. The dark or non-reflective surface reduces light scatter inside the eye, which may cause image degradation, patient discomfort, and/or a cosmetically objectionable mirror-like surface in the pupil of the patient when the patient's pupil is dilated, for example in a low light environment. A similar treatment, for the same reasons, may be applied to the optic ring and haptics.

In an embodiment, the ring-shaped plate 255 has three separate functions. A pericentric zone 260, located underneath the flexion zone 160 of the anterior capsule functions as an artificial iris to block peripheral stray light and prevent image distortion and degradation through the flexion and fusion zones of the optic 105. The size of the hole in the center of the ring-shaped plate 255 becomes an effective pupil, allowing only light traveling through the optical zones of the optic 105 to reach the patient's retina. The size of the hole preferably generally matches the diameter of the optical zones and may be, for example, 4 to 7 mm in diameter, to allow the maximum amount of non-distorted light to pass through to the retina.

Immediately peripheral to the pericentric zone 260 is disposed a restraining zone 265 that defines one or more rings of concentric restraining holes 270 sized and distributed to facilitate restraining the haptic in a disaccommodated position at implantation and several weeks thereafter, described below. Accordingly, the restraining holes 270 extend through the anterior capsule, holes defined in the ring-shaped plate 255, and the posterior capsule, or may be completely covered by a continuous layer of silicone elastomer. The restraining holes 270 preferably have a diameter of 100 to 500 microns, and are spaced 50 to 200 microns apart. Preferably, at least 2-4 holes are disposed in a vicinity of each peg 240. The ideal number and size of the restraining holes 270 have been discussed above. The remainder of the holes 270, not in position to restrain the haptic arms 115, are generally larger to allow for more adhesive contact between the fusion zones of the anterior and posterior optic while maintaining structural integrity of the plate 255 and not allowing too much stray light to travel to the back of the eye.

The haptics 100 in this embodiment are zonular capture haptics made of shape memory metal, such as nitinol, and can be as thin as 0.002". The arms of the haptics 115 move in the same plane with the fusion zone, which corresponds to the plane of axial pull by zonules in the closed and fused capsular bag. The individual haptics 100 allow room for radial capsular sectioning between the haptics 100. The flexion zone of the haptic 110 is short and at a relatively steep angle to allow the haptic peg rings 245 to approach the optic pegs 240 for fixation. The optic peg rings may be circular or a different shape, generally matching the shape of the pegs 240, and sized to make a tight fit or squeeze on the pegs 240. Cross bars 275 on the haptic arms 115 allow restraining of the haptics 100 to a disaccommodated configuration by suturing across the optic fusion zone, through the restraining holes, as described below. In addition to the restraining function, the holes allow direct contact between the anterior and posterior capsules and with bonding material to form a more secure fusion of the anterior and posterior optics. The short and steep flexion zones 110 of the haptic 100 convert most of the radial zonular pull into a shape shifting effect on the optic 105 with a smaller effect towards an axial shift of the optic 105. The distal portion of each haptic 100 has a sinusoidal shape 125 to allow this end of the haptic 100 to expand and contract circumferentially and in step with the change in diameter of the capsular bag during accommodation and disaccommodation, so that the haptic 100 does not impede the movement of the fused capsular bag. For a similar reason, the two proximal ends of each haptic 100, attached to the pegs of the optic 105, are not connected to each other. Rather, the proximal haptic ends form an open loop, so that the pegs and haptic ends can move to a larger diameter when the anterior capsule stretches during disaccommodation. The haptic 100 is shape set for the accommodated configuration.

In use, a suture is passed across the fused, silicone peripheral capsules, through the restraining holes, and around each cross bar 275 on the arm of the haptic 115 to create a loop to immobilize the haptic 100 in stretched disaccommodated position. The suture may be made from any biocompatible material known in the art. Such a suture may be cut by non-invasive external laser application, such as YAG or femtosecond laser. The cut suture segments may be trapped in the silicone fusion zone and may not necessarily be removed from the eye. Once the suture is cut, the haptic 100 is free to move.

The third purpose of the embedded plate 255 is to enhance the structural stability and shape memory of the flexible silicone optic, to ensure that it returns to a desired shape after compression or deformation during the implantation step, for example by being forced to go through a small incision injector. Similarly, an optic 105 sufficiently thin to be shape shifted by weak zonular forces has some preferred areas of stable geometry during haptic movement, to direct all movement energy to the accommodating element and not the reminder of the flexible optic.

In the embodiment illustrated in FIGS. 12A-12C, during disaccommodation, the radial pull of the zonules is converted mostly to a radial pull of the haptics, which is conveyed to the pegs on the flexion zone of the optic. This radial pull flattens the optical zone to reduce its optical power by increasing the diameter of the optical zone. The optic is filled with a fluid having a high index of refraction fluid, as silicone oil, in a resting accommodated shape. A preferred index of refraction of the fluid is, e.g., at least 1.30 to 1.55. The greater the refractive index, the more accommodative power is provided for a smaller change in shape. However, this may result in greater viscosity which could make movement more difficult, or in a chemical composition which may not be compatible with the optic vesicle polymer over several decades. Since the volume of fluid in the optic vesicle is constant, the anterior capsule will stretch to increase its surface area, to reach the volume/surface area ratio required by the geometry of a flatter optic. The anterior capsule is very thin to allow for this stretch to occur below the disaccommodative load level that can be generated by the eye. When ciliary body contraction neutralizes the radial pull of the zonules, the shape memory of both the optic and the haptic reshape the optic to a more convex shape and a more anterior location, thereby increasing its power, by as much as 10-15 diopters.

The AD-IOL is manufactured from four separate components that are assembled together. The two optics elements (anterior and posterior capsules) are molded as individual components from silicone elastomer or a similar biocompatible material. The individual haptics and the ring plate are laser cut from a nitinol sheet of desired thickness, which can be as thin as 0.002-0.001 inches. The haptic is heat shaped to its accommodated configuration. The surface of the nitinol parts is chemically treated to increase biocompatibility and remove any laser-induced irregularities, for example by a chemical or electrochemical pickling or oxidizing bath or other processes known in the art. The ring plate is positioned in place in the posterior optic element with a bonding material in the fusion zone, such as uncured silicone elastomer or silicone adhesive. Additional bonding agent is added and the anterior capsule is added with the overhanging lip covering the seam between the ring plate and the posterior optic capsule. The three components are clamped and heat treated to cure the bonding material. A needle enters the optic tangentially through the fusion zone, and silicone oil is injected into the central cavity; any air bubbles are meticulously removed. The silicone fill is adjusted to achieve the desired optical power with minimal or no stretching of the thin anterior capsule. When the needle is removed, the external ostium of the self-sealing needle passage is further sealed with bonding material. The haptic is placed in position by grasping the optic pegs and pulling them through the corresponding holes in the haptics. Additional bonding material is applied as a mushroom cap to the pegs, or the optic rings can be secured with miniature rivets, sutures, or other devices know in the art. Alternatively, the optic vesicle is manufactured as a single piece by rotation molding or a similar technique and the ring plate is fused externally to either the posterior or anterior fusion zone.

Figure 13:
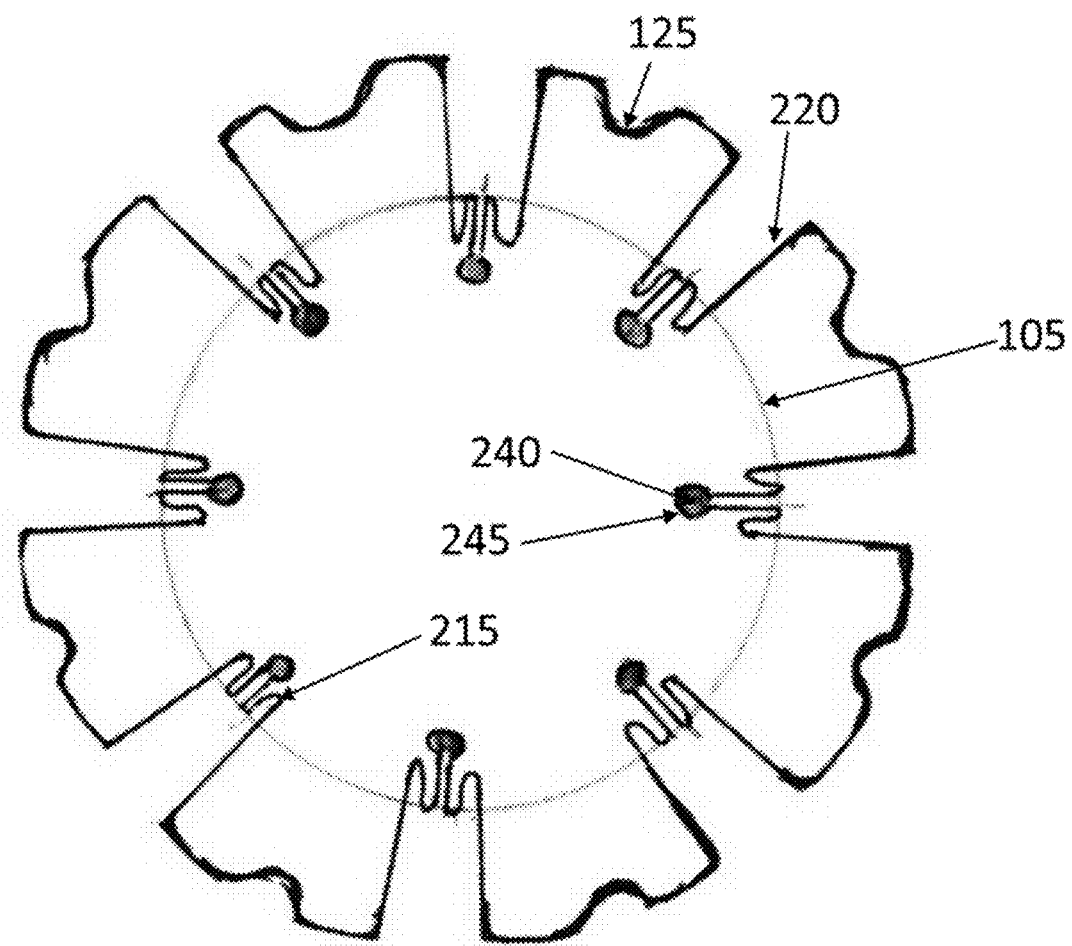
FIG. 13 is a schematic drawing of a configuration for a continuous nitinol wire haptic adapted to work with the dual mode AD-IOL of FIG. 12C.

An alternative haptic configuration uses a continuously looped nitinol wire, with loops capturing the attachment optic pegs, restraining holes and equator of the capsular bag in patterns similar to intravascular stents. This continuous loop haptic makes contact with more points in the equator of the fused capsular bag and distributes uneven lateral loads throughout the haptic system to decrease the risk of optical distortion of the very thin anterior capsule. In particular, referring to FIG. 13, a continuous loop nitinol wire haptic 220 may be adapted to work with the dual mode AD-IOL of FIG. 12C. The haptic has loops 245 to capture the optic pegs 240, openings or notches 215 for receiving a restraining device proximate the fusion zone of the optic 105 and a sinusoidal equatorial region 125 adapted to change diameter in synchrony with the capsular bag. The haptic is shape set to cooperate with the elastic recoil of the flexible optic and allow for accommodation and disaccommodation to take place under the force load produced in the eye. The continuous loop of the haptic allows for uniform distribution of lateral or irregular circumferential stresses on the haptic, as they may occur after capsular bag closure and fibrosis, and such to minimize irregular distortion of the flexible optic.

Figure 14:
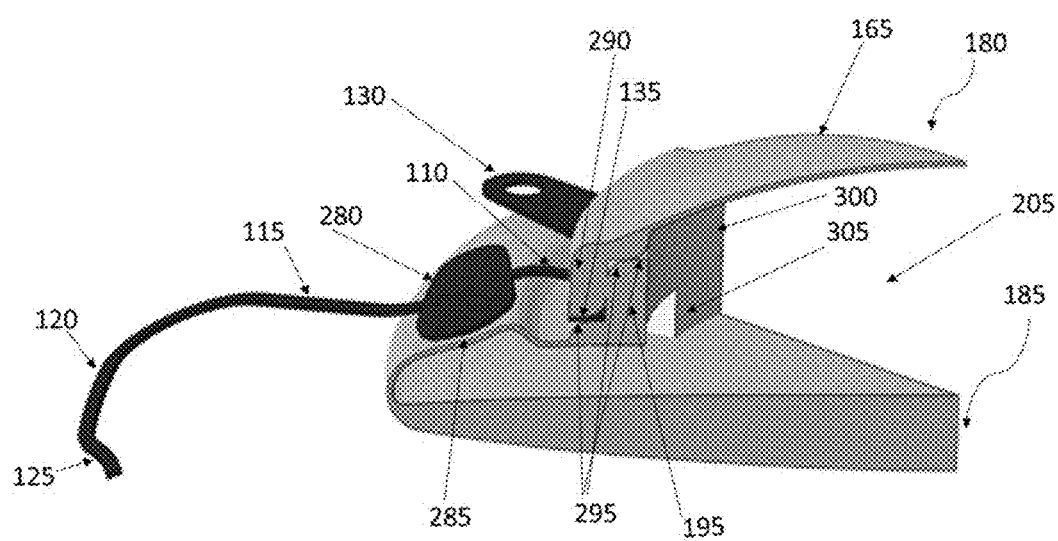
FIG. 14 is a CAD-generated image of a section through a dual mode AD-IOL in accordance with embodiments of the invention, in which paddle-like structures on the arms of the haptics press on thin zones of the optic vesicle to direct the fluid to the anterior optical surface, which provided increased power during accommodation. The posterior optical surface is more rigid and conveys the prescription refractive power.

FIG. 14 is a CAD-generated image of a section through an alternative dual mode AD-IOL. This embodiment utilizes a flexible optic made from an anterior 180 and a posterior 185 capsule fused together and a haptic system configuration, essentially similar to the one in FIG. 5. This haptic configuration has been proven to capture the movement amplitude and dynamics in the eyes of a Rhesus monkey experimental model over extended periods of time, in a fibrosed and fused capsular bag, and to convert that movement into a maximal axial shift.

The haptic system includes an optic ring 135, radially extending restraining tabs 130 and radially extending closed looped haptics. Each haptic 100 has an equatorial region 120 that becomes captured in the fused capsular bag, and has a generally sinusoidal shape 125 to allow this end of the haptic 100 to expand and contract circumferentially and in step with the change in diameter of the capsular bag during accommodation and disaccommodation, so that the haptic 100 does not impede the movement of the fused capsular bag. Proximal to the equatorial region are radial arms 115 and then a flexion zone 110 that attaches them to the optic ring. The haptics 100 are shaped set to be angled posteriorly, as much as at 45 degrees in resting position. In contrast to the haptic structure depicted in FIGS. 5A and 5B, this embodiment has fewer restraining tabs, thereby allowing room for wide paddle-like structures 280, attached to the radial arms 115 that overlay compression zones 285 in the optic 105 and can exert pressure on these thin zones of the optic vesicle to shift fluid during accommodation. The paddle-like structures 280 may be made from nitinol, preferably from the same sheet and same thickness as the remainder of the haptic system, and have dimensions of, e.g., 100×500 microns, to encompass as much of the optic flexion zone 110 as possible. If necessary, the paddle 280 can be stiffened by addition of additional material bonded to it, or by folding over some of the same material, and can be shape set to the curvature of the optic 105, to drive as much fluid as possible.

The anterior capsule 180 includes a central optical zone 165 and a thicker fusion zone 290 in the periphery, adapted to bond to the fusion zone of the posterior optic. The fusion zones have rounded edges to create channels or spaces 295 where excess bonding material can bead and collect rather than spread toward the optical surface. The central anterior capsule is made of shape memory silicone elastomer and may be as thin as 25-50 microns. The thickness of the optical zone may be uniform throughout or change gradually from the center to the periphery. The anterior capsule provides the accommodative component of the IOL.

The posterior capsule 185 is substantially thicker, to resist distortion during accommodation, and it also has a central optical zone 200 and a peripheral fusion zone 195. The fusion zone has similar rounded edges to allow excess bonding material to bead in circumferential spaces 295 and not spread toward the optical surface or haptic arms 115. The optical zone carries the patient's prescription power, the power needed to correct the patient's aphakic refractive error including possibly astigmatic error. The axis of the astigmatic correction is marked externally. The anterior equatorial zone of the posterior capsule has compressible 285 and non-compressible 300 zones. The compressible zones 285 are immediately below the paddle 280 elements of the haptics 100 and are very thin, so that they can be easily squeezed by the haptics 100. The non-compressible zones 300 are located under the restraining tabs of the haptic 100. Here, the equatorial zones of the anterior and posterior capsules are fused with pillars or ribs 305. This imparts structural rigidity to the posterior optical surface when pressure is applied by haptics 100 to the compressible zones 295.

In this embodiment, zonular axial pull causes flattening of the haptic structure and posterior axial shift. When the zonular tension abates, the haptics 100 flex posteriorly towards the visual axis and axially shift the optic anteriorly and also shape shift the optic geometry. The flexible optic of this embodiment is fluid filled and adapted to change to a more accommodated, convex configuration of the thin anterior optic capsule when the haptics 100 press on thin peripheral compression zones shifting fluid centrally and anteriorly. The surface area of the thin anterior optic capsule, the accommodating element, may be altered, or stretched during accommodation, when additional volume of fluid is shifted be the haptics 100 compression and the optical zone becomes more spherical. These changes maintain the proper volume/surface area ratio required by the geometry of the accommodated optic 105. The thickness of the compression zones may be as little as 25-50 microns, and the compression zone may be thinner and more stretchable than the anterior optical zone.

The internal cavity 205 is filled with fluid having a greater index of refraction than water, such as silicone oil for example, and preferably with the same index of refraction as the elastomer used for the anterior and posterior capsule elements. The cavity 205 is filled to its disaccommodated shape, where the optical zone is generally not stretched but the compression zones may or may not be stretched, depending on their thicknesses and desired balance of opposing forces. Biocompatible sutures or rings are used to suspend the haptics 100 to the restraining tabs, giving the haptics 100 a generally horizontal configuration, in the same plane with the optic ring and the closed capsular bag prior to implantation. The sutures or rings are amendable to being sectioned by an external, non-invasive laser, such as YAG or femtosecond. After several weeks post implantation, once the capsular bag has closed, fused and fibrosed, trapping the haptics within, the suture or ring is cut and radial cuts in the capsular bag may also be performed between haptics 100. This allows the haptic system to move in response to zonular tension. During accommodation, the zonular tension abates, the haptics 100 can move towards their resting state, vaulting posteriorly and compressing the compression zones in between. This compression shifts the internal fluid centrally and forward and bows the anterior optical surface to a more convex, accommodated configuration. When zonular tension resumes during disaccommodation, the haptics 100 are pulled apart and the stretch of the anterior optical zone pushes fluid down and out and fills the compression zones.

The two optical components are made of shape memory elastomer, such as silicone, and preferably of a different silicone family than the fluid filling the optic vesicle. They are molded separately and assembled together with the haptic ring and bonded. The fusion zones ensure both centration of the two optical components and also the trapping of the optic ring between the two optical components, which helps to stabilize the structure of the IOL.

The haptic system is made of nitinol, laser cut from a sheet that may be as thin as 0.0001" or 0.0002", shape set to its resting accommodated configuration and chemically surface treated to increase its biocompatibility and reduce laser induced irregularities. Once the three components are assembled and bonded, the cavity is filled with fluid, such as silicone oil, with a needle passing tangentially through a thicker area of the lens.

While several aspects of the present invention have been described and depicted herein, alternative aspects may be effected by those skilled in the art to accomplish the same objectives. Accordingly, it is intended that the appended claims cover all such alternative aspects as fall within the true spirit and scope of the invention.

What is claimed is:

1. A dual mode accommodative-disaccommodative intraocular lens (dual mode AD-IOL) comprising:
   a haptic system comprising a plurality of closed-loop haptics having shape memory;
   a shape-shifting flexible optic comprising an anterior optic capsule and a posterior optic capsule, each of the two capsules comprising a fusion zone and the fusion zones of the two capsules being fused together, thereby defining therebetween an optic vesicle, the optic vesicle being filled with a fluid, wherein (i) the haptics are attached to the optic, allowing an action of the haptics to alter a shape of the optic, (ii) the shape-shifting flexible optic has a diameter of ≤8 mm and (iii) the dual mode AD-IOL, at rest, is in a fully accommodated configuration as a result of at least one of the shape memory of the haptic system and a shape-shifting capability of the flexible optic; and
   a restraining component sized and configured to immobilize the haptic in at least one of a flatter angle and a larger diameter in a disaccommodated configuration of the AD-IOL, when compared to the accommodated configuration.

2. The dual-mode ID-IOL of claim 1, wherein the closed-loop haptics are at least one of trapezoidal and T-shaped.

3. The dual-mode AD-IOL of claim 1, further comprising:
   an optic ring,
   wherein the optic ring connects the haptics to each other and to the optic.

4. The dual-mode AD-IOL of claim 1, wherein the haptics are attached to the optic by a portion of each haptic being embedded in the optic at the fusion zone.

5. The dual-mode AD-IOL of claim 1, wherein each closed-loop haptic is configured to adapted to transmit to the optic radial pull created by zonular tension during disaccommodation of the AD-IOL.

6. The dual-mode AD-IOL of claim 1, wherein each closed-loop haptic is configured to adapted to return to a set shape during accommodation of the AD-IOL.

7. The dual-mode AD-IOL of claim 1, wherein the restraining component is selected from the group consisting of a restraining tab disposed on a haptic or an optic ring, a restraining hole defined by a haptic portion, a restraining hole defined by an optic in a fusion zone thereof, a cross bar on a haptic arm, a restraining ring, and a suture.

8. The dual-mode AD-IOL of claim 1, further comprising a ring-shaped plate embedded between an anterior optic capsule and a posterior optic capsule of the optic.

9. The dual-mode AD-IOL of claim 1, wherein each of the closed-loop haptics comprises a first connecting feature and the optic comprises a second connecting feature adapted to engage with the first connecting feature.

10. The dual-mode AD-IOL of claim 1, wherein each of the closed-loop haptics is shape set to contribute to axial shift and shape shift of the optic.

11. The dual-mode AD-IOL of claim 1, wherein the haptic system comprises at least two optic rings, each optic ring comprising two closed-loop haptics, the optic rings being disposed over the optic and configured to rotate to overlay the haptics of a first optic ring over the haptics of a proximate optic ring, to reduce a profile thereof to facilitate loading of the dual-mode AD-IOL in an injector.

12. The dual-mode AD-IOL of claim 1, wherein at least one closed-loop haptic comprises a radial segment and a paddle being disposed on the radial segment configured to compress a portion of the optic.

13. The dual-mode AD-IOL of claim 1, wherein a sum of at least an accommodative memory or a disaccommodative memory of the optic and the haptic system is less than 1 gram force.

14. The dual-mode AD-IOL of claim 1, wherein the anterior and posterior optic capsules are fused with a bonding material and the fusion zone defines a channel configured to receive excess bonding material.

15. The dual-mode AD-IOL of claim 1, wherein a change in a shape of the flexible optic changes a ratio of a surface area of the optic vesicle to a volume of the optic vesicle and the haptic system changes size and shape to accommodate the change in the ratio.

16. The dual-mode AD-IOL of claim 1, wherein one of the optic capsules comprises a thick, rigid optical zone carrying a fixed refractive power including astigmatic correction, a thickness of the thick rigid optical zone being selected from a range of 200 to 500 microns with the thickness being greater than a thickness of a flexion zone disposed proximate the thick, rigid optical zone.

17. The dual-mode AD-IOL of claim 1, wherein one of the optic capsules comprises a thinner, more easily distorted flexion zone disposed proximate a central optical zone.

18. The dual-mode AD-IOL of claim 1, wherein the optic vesicle has shape memory.

19. The dual-mode AD-IOL of claim 1, wherein the haptic system is adapted to fit within an IOL injection system.

20. A method for implanting a dual-mode accommodative-disaccommodative intraocular lens (AD-IOL), comprising the steps of:

providing an AD-IOL comprising:
    a haptic system comprising a plurality of closed-loop haptics having shape memory;
    a shape-shifting flexible optic comprising an anterior optic capsule and a posterior optic capsule, each of the two capsules comprising a fusion zone and the fusion zones of the two capsules being fused together, thereby defining therebetween an optic vesicle, the optic vesicle being filled with a fluid, wherein (i) the haptics are attached to the optic, allowing an action of the haptics to alter a shape of the optic, (ii) the shape-shifting flexible optic has a diameter of ≤8 mm and (iii) the dual mode AD-IOL, at rest, is in a fully accommodated configuration as a result of at least one of the shape memory of the haptic system and a shape-shifting capability of the flexible optic; and
    a restraining component sized and configured to immobilize the haptic in at least one of a flatter angle and a larger diameter in a disaccommodated configuration of the AD-IOL, when compared to the accommodated configuration;
implanting the AD-IOL into an eye of a patient;
allowing a capsular bag of the eye to fuse through the haptics; and
releasing the haptics by making radial cuts therebetween, the radial cuts extending from edges of the eye's anterior capsule towards an equator of the eye's capsular bag for a distance defined to produce a desired amount of release in stiffness of the eye's fibrosed capsular bag.

* * * * *